(12) United States Patent
Heuer et al.

(10) Patent No.: US 7,101,539 B2
(45) Date of Patent: Sep. 5, 2006

(54) USE OF LP82 TO TREAT HEMATOPOIETIC DISORDERS

(75) Inventors: Josef Georg Heuer, Indianapolis, IN (US); Ling Liu, Carmel, IN (US); Timothy W. Noblitt, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 256 days.

(21) Appl. No.: 10/467,431

(22) PCT Filed: Feb. 14, 2002

(86) PCT No.: PCT/US02/03377

§ 371 (c)(1), (2), (4) Date: Aug. 6, 2003

(87) PCT Pub. No.: WO02/070001

PCT Pub. Date: Sep. 12, 2002

(65) Prior Publication Data

US 2004/0092445 A1 May 13, 2004

Related U.S. Application Data

(60) Provisional application No. 60/272,242, filed on Feb. 14, 2002, provisional application No. 60/353,789, filed on Feb. 1, 2002, provisional application No. 60/332,740, filed on Nov. 19, 2001.

(51) Int. Cl.
- A61K 38/18 (2006.01)
- A61K 38/20 (2006.01)
- C07K 14/475 (2006.01)
- C07K 14/54 (2006.01)

(52) U.S. Cl. .............. 424/85.1; 424/198.1; 514/2; 514/12; 530/300; 530/351; 530/399

(58) Field of Classification Search .............. None
See application file for complete search history.

(56) References Cited

U.S. PATENT DOCUMENTS 6,576,743 B1 * 6/2003 Conklin et al. ............ 530/351
6,610,286 B1 * 8/2003 Thompson et al. ........ 424/85.2

FOREIGN PATENT DOCUMENTS

WO  WO 9927103   6/1999
WO  WO 00/12708  3/2000

OTHER PUBLICATIONS

Liu et al. Selective enhancement of multipotential hematopoietic progenitors in vitro and in vivo by IL-20. Blood 102(9): 3206-3208, 2003.*
Xu et al. Interleukin-20. Int Immunopharmacol 4: 627-633, 2004.*
Rich et al. IL-20-a new effector in skin inflammation. Curr Biol 11: R531-R534, 2001.*
Quesenberry et al., "Hematopoietic Stem Cells, Progenitor Cells, and Cytokines", pp. 153-174, Williams Hematology, Sixth Edition, New York: McGraw-Hill, 2001.*
Elgert, K. Immunology, understanding the immune system. New York: Wiley-Liss, Inc., 1996, pp. 304, 324-326.*
Geisler and Wagner, Zytokinkombinationen für die In-vivo-und Ex-vivo-Expansion hämatopoetischer Progenitorzellen, Acta Med. Austriaca 2000, 27 (Supplement No. 52) :21-24.
Blumberg H. et al. Interleukin 20: discovery, receptor identification, and role in epidermal function. *Cell.* 104(1) :9-19, Jan. 12, 2001.
Broxmeyer, Hal E., et al., "Regulation of hematopoiesis in a sea of chemokine family members with a plethora of redundant activities", Experimental Hematology, 1999, pp. 1113-1123, vol. 27, No. 7.
Goldman, Samuel J., "Preclinical Biology of Interleukin 11: A Multifunctional Hematopoietic Cytokine with Potent Thrombopoietic Activity", Stem Cells, 1995, pp. 462-471, vol. 13.

* cited by examiner

*Primary Examiner*—Elizabeth Kemmerer
*Assistant Examiner*—Bridget E. Bunner
(74) *Attorney, Agent, or Firm*—MaryAnn Wiskerchen

(57) ABSTRACT

The present invention relates to a method of using a mammalian gene sequence and polypeptides encoded thereby to treat mammalian hematopoietic disorders. More specifically the present invention relates to methods of using compositions comprising at least one LP82 agonist, LP82 antagonist, LP82 polynucleotide, LP82 polypeptide, and/or LP82 antibody for the prevention and/or treatment of mammalian hematopoietic disorders, including, but not limited to, anemia, leukemia, and hematopoietic conditions caused by bone marrow transplantation or chemo-/radiation therapy.

13 Claims, 2 Drawing Sheets

SEQUENCE LISTING

<160> NUMBER OF SEQ ID NOS: 5

<210> SEQ ID NO 1
<211> LENGTH: 867
<212> TYPE: DNA
<213> ORGANISM: Homo sapiens
<220> FEATURE:
<221> NAME/KEY: CDS
<222> LOCATION: (272)..(799)
<223> OTHER INFORMATION:
<220> FEATURE:
<221> NAME/KEY: sig_peptide
<222> LOCATION: (272)..(325)
<223> OTHER INFORMATION:

<400> SEQUENCE: 1

```
gccgccagtg tgatggatat ctgcagaatt cgcccttga aacaggctcc taggagacca      60
gaagcagcag cctttcctga gctcagtgcc tgctgttcca ggccttacct gctgggcact     120
aacggcggag ccaggatggg gacagaataa aggagccacg acctgtgcca ccaactcgca     180
ctcagactct gaactcagac ctgaaatctt ctcttcacgg gaggcttggc agttttctt      240 actcctgtgg tctccagatt tcaagcctaa g atg aaa gcc tct agt ctt gcc        292
                                   Met Lys Ala Ser Ser Leu Ala
                                   1               5 ttc agc ctt ctc tct gct gcg ttt tat ctc cta tgg act cct tcc act       340
Phe Ser Leu Leu Ser Ala Ala Phe Tyr Leu Leu Trp Thr Pro Ser Thr
        10                  15                  20 gga ctg aag aca ctc aat ttg gga agc tgt gtg atc gcc aca aac ctt       388
Gly Leu Lys Thr Leu Asn Leu Gly Ser Cys Val Ile Ala Thr Asn Leu
25                  30                  35 cag gaa ata cga aat gga ttt tct gag ata cgg ggc agt gtg caa gcc       436
Gln Glu Ile Arg Asn Gly Phe Ser Glu Ile Arg Gly Ser Val Gln Ala
40                  45                  50                  55 aaa gat gga aac att gac atc aga atc tta agg agg act gag tct ttg       484
Lys Asp Gly Asn Ile Asp Ile Arg Ile Leu Arg Arg Thr Glu Ser Leu
                60                  65                  70 caa gac aca aag cct gcg aat cga tgc tgc ctc ctg cgc cat ttg cta       532
Gln Asp Thr Lys Pro Ala Asn Arg Cys Cys Leu Leu Arg His Leu Leu
            75                  80                  85 aga ctc tat ctg gac agg gta ttt aaa aac tac cag acc cct gac cat       580
Arg Leu Tyr Leu Asp Arg Val Phe Lys Asn Tyr Gln Thr Pro Asp His
        90                  95                  100 tat act ctc cgg aag atc agc agc ctc gcc aat tcc ttt ctt acc atc       628
Tyr Thr Leu Arg Lys Ile Ser Ser Leu Ala Asn Ser Phe Leu Thr Ile
    105                 110                 115 aag aag gac ctc cgg ctc tgt cat gcc cac atg aca tgc cat tgt ggg       676
Lys Lys Asp Leu Arg Leu Cys His Ala His Met Thr Cys His Cys Gly
120                 125                 130                 135 gag gaa gca atg aag aaa tac agc cag att ctg agt cac ttt gaa aag       724
Glu Glu Ala Met Lys Lys Tyr Ser Gln Ile Leu Ser His Phe Glu Lys
                140                 145                 150 ctg gaa cct cag gca gca gtt gtg aag gct ttg ggg gaa cta gac att       772
Leu Glu Pro Gln Ala Ala Val Val Lys Ala Leu Gly Glu Leu Asp Ile
            155                 160                 165 ctt ctg caa tgg atg gag gag aca gaa taggaggaaa gtgatgctgc             819
Leu Leu Gln Trp Met Glu Glu Thr Glu
        170                 175 tgctaagaat attcgaggtc aaagggcgaa ttccagcaca ctggcggc                  867
```

```
<210> SEQ ID NO 2
<211> LENGTH: 176
<212> TYPE: PRT
<213> ORGANISM: Homo sapiens

<400> SEQUENCE: 2

Met Lys Ala Ser Ser Leu Ala Phe Ser Leu Leu Ser Ala Ala Phe Tyr
  1               5                  10                  15

Leu Leu Trp Thr Pro Ser Thr Gly Leu Lys Thr Leu Asn Leu Gly Ser
                 20                  25                  30

Cys Val Ile Ala Thr Asn Leu Gln Glu Ile Arg Asn Gly Phe Ser Glu
             35                  40                  45

Ile Arg Gly Ser Val Gln Ala Lys Asp Gly Asn Ile Asp Ile Arg Ile
         50                  55                  60

Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
                 85                  90                  95

Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Cys His Ala
            115                 120                 125

His Met Thr Cys His Cys Gly Glu Glu Ala Met Lys Lys Tyr Ser Gln
        130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Thr Glu
                165                 170                 175

<210> SEQ ID NO 3
<211> LENGTH: 176
<212> TYPE: PRT
<213> ORGANISM: Homo sapiens
<220> FEATURE:
<221> NAME/KEY: MISC_FEATURE
<222> LOCATION: (48)..(48)
<223> OTHER INFORMATION: X aa at position 48 is Asp or Glu
<220> FEATURE:
<221> NAME/KEY: MISC_FEATURE
<222> LOCATION: (126)..(126)
<223> OTHER INFORMATION: Xaa at position 126 is Ser or Cys

<400> SEQUENCE: 3

Met Lys Ala Ser Ser Leu Ala Phe Ser Leu Leu Ser Ala Ala Phe Tyr
  1               5                  10                  15

Leu Leu Trp Thr Pro Ser Thr Gly Leu Lys Thr Leu Asn Leu Gly Ser
                 20                  25                  30

Cys Val Ile Ala Thr Asn Leu Gln Glu Ile Arg Asn Gly Phe Ser Xaa
             35                  40                  45

Ile Arg Gly Ser Val Gln Ala Lys Asp Gly Asn Ile Asp Ile Arg Ile
         50                  55                  60

Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
                 85                  90                  95

Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Xaa His Ala
            115                 120                 125
```

```
                                  -continued

His Met Thr Cys His Cys Gly Glu Glu Ala Met Lys Lys Tyr Ser Gln
        130             135             140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                    165                 170                 175

<210> SEQ ID NO 4
<211> LENGTH: 38
<212> TYPE: DNA
<213> ORGANISM: Synthetic Nucleotides

<400> SEQUENCE: 4
ttggcgcgcc atccaccatg aaagcctcta gtcttgcc                           38

<210> SEQ ID NO 5
<211> LENGTH: 60
<212> TYPE: DNA
<213> ORGANISM: Synthretic Nucleotides

<400> SEQUENCE: 5
tagcggccgc tacttgtcgt cgtcatcctt gtagtcttct gtctcctcca tccattgcag   60
```

USE OF LP82 TO TREAT HEMATOPOIETIC DISORDERS

This is the national phase application, under 35 USC 371, for PCT/US02/03377, filed Feb. 14, 2002, which claims the priority of U.S. provisional application Nos. 60/272,242 filed Feb. 28, 2001; 60/332,740 filed Nov. 19, 2001 and 60/353,789 filed Feb. 1, 2002.

FIELD OF THE INVENTION

The present invention relates to recombinant DNA technology as applied to the field of human medicine. In particular, the invention relates to new methods of treating or preventing mammalian hematopoietic disorders including, but not limited to, anemia, that comprise the administration of LP82, a recently identified interleukin-like polypeptide. Additionally, new methods of treating or preventing mammalian hematopoietic disorders including, but not limited to, leukemia that comprise the administration of antibodies and other agents that neutralize or antagonize LP82 activity are disclosed herein.

BACKGROUND OF THE INVENTION

Hematopoiesis is an essential, lifelong process whereby highly specialized blood cells are generated from hematopoietic stem cells, including cells responsible for carbon dioxide and oxygen transport (erythrocytes), blood clotting (platelets), humoral immunity (B lymphocytes), cellular immunity (T lymphocytes), as well as cells which respond to foreign organisms and their products (granulocytes, monocytes, and macrophages). All of these cells can be functionally divided into two distinct groups termed myeloid and lymphoid. During normal human adult life, myeloid cells are produced exclusively within the bone marrow (Lichtman, M. A., *Exp.Hematol.* 9:391, 1981) while cells of the lymphoid lineage are produced to varying degrees in the bone marrow, spleen, thymus, and lymph nodes. Mature functional end cells and their immediate precursors have a limited life-span and a limited proliferative capacity and hence are not self-maintaining. Thus, these cells are continuously replaced from a pool of more primitive proliferating progenitor cells. Ultimately, all cells of both the myeloid and lymphoid lineage are derived from totipotent stem cells. In the normal human adult it is estimated that approximately 200 billion erythrocytes (Erslev, A. J., *Hematology*, McGraw-Hill, New York, 1983) and 60 billion neutrophilic leukocytes (Dancey, J. T. et al, *J. Clin. Invest.* 58:705, 1976) are produced everyday.

Hematopoiesis is necessarily tightly regulated. The molecules responsible for regulating various aspects of hematopoiesis can generally be divided into two groups: extracellular growth factors and intracellular factors (e.g. growth factor receptors, signaling molecules and transcriptional factors). Hematopoietic cytokines have been successfully used to treat various diseases arising from imbalances between degradation and reconstitution of blood cells or from generation of inappropriate numbers of certain blood cells. For example, recombinant erythropoietin (EPO) is a glycoprotein administered for the treatment of anemia in chronic renal failure patients, zidovudine-treated HIV-infected patients, cancer patients on chemotherapy, and patients receiving autologous transfusions. Recombinant thrombopoietin (TPO) is currently undergoing clinical evaluation for treatment of thrombocytopenia. In spite of the availability of EPO and TPO, there remains a need to provide additional methods of altering the hematopoietic state of an individual. Accordingly, it is an object of the present invention to provide novel methods of treatment that can prevent and/or correct an undesired hematopoietic condition in a patient.

SUMMARY OF THE INVENTION

A new member of the interleukin family was described in international patent applications WO99/27103 and WO00/12708 (the contents of each are incorporated herein by reference) and alternatively named human Zcyto10 and PRO1801, respectively. This protein, hereinafter referred to as LP82, exhibits the four alpha helix structure typical of known cytokines and shares significant homology with IL-10 and IL-19.

The present invention embodies a method for modulating hematopoiesis, including erythropoiesis (production of red blood cells), leukopoiesis (production of white blood cells) and/or thrombocytopoiesis (production of platelets) that comprises administering a therapeutically-effective amount of at least one LP82 agonist, LP82 antagonist, LP82 polynucleotide, LP82 polypeptide, LP82 functional fragment, LP82 variant or LP82 antibody, as defined herein, to a cell, tissue, organ, mammal, human or patient in need of such therapy.

The invention embodies a method for increasing the number of one or more types of hematopoietic progenitor cells, preferably CFU-GEMM, CFU-MK, CFU-GM, BFU-E and/or megakaryocyte cells, most preferably CFU-GEMM cells, that comprises administering a therapeutically effective amount of at least one LP82 polypeptide or variant thereof, LP82 polynucleotide, LP82 agonist or LP82 functional fragment to a cell, tissue, organ, mammal, human or patient in need of such therapy.

It is contemplated that all methods of the invention may further comprise administration of a therapeutically effective amount of at least one hematopoietic cytokine or hematopoietic cytokine antibody in addition to administration of LP82. The hematopoietic cytokine(s) preferred are erythropoietin ("Epo"), thrombopoietin ("TPO"), IL-1, IL-3, IL-4, IL-5, IL-6, IL-7, IL-9, IL-11, granulocyte colony stimulating factor ("G-CSF"), granulocyte-macrophage-colony stimulating factor ("GM-CSF"), macrophage-colony stimulating factor ("M-CSF") and/or stem cell factor ("SCF"), most preferably Epo, IL-3, SCF, G-CSF and/or GM-CSF. It is contemplated that the hematopoietic cytokine may be administered prior to, simultaneously with, and/or subsequent to administration of LP82. It is further contemplated that the methods of the invention may be performed simultaneously with, subsequent to or prior to administration of a chemotherapy or radiation therapy.

The invention further embodies a method of increasing at least two types of mature hematopoietic cells in a mammal, preferably a human, in need thereof comprising administering to said mammal a therapeutically effective amount of LP82 polypeptide or a variant thereof as defined herein, optionally also administering a therapeutically effective amount of at least one hematopoietic cytokine in addition to LP82 administration.

The invention still further embodies a method of increasing red blood cells in a mammal, preferably a human, in need thereof, comprising administering to said mammal a therapeutically effective amount of an LP82 polypeptide or a variant thereof as defined herein, optionally also administering a therapeutically effective amount of at least one hematopoietic cytokine in addition to the LP82 polypeptide.

It is contemplated that the at least one hematopoietic cytokine may be administered prior to administration of LP82, simultaneously with administration of LP82 and/or subsequent to administration of LP82.

The invention also embodies a method of increasing hematocrit in a mammal, preferably a human, in need thereof, comprising administering to said mammal a therapeutically effective amount of an LP82 polypeptide or a variant thereof as defined herein.

The invention further embodies a method for increasing the percentage of one or more types of hematopoietic progenitor cells, preferably CFU-GEMM cells, in a mammal, human, or patient that are in the S-phase of the cell cycle that comprises administering a therapeutically effective amount of at least one LP82 polypeptide, LP82 polynucleotide, LP82 agonist, LP82 functional fragment or LP82 variant, as defined herein, to a cell, tissue, organ, mammal, human or patient in need of such therapy. It is contemplated that the method may further comprise administering a therapeutically-effective amount of at least one hematopoietic cytokine in addition to LP82 administration. It is contemplated that the at least one hematopoietic cytokine may be administered prior to administration of LP82, simultaneously with administration of LP82 and/or subsequent to administration of LP82.

The invention further embodies a method for increasing the number of one or more types of lymphoid cells that comprises administering a therapeutically effective amount of an LP82 polypeptide.

The invention further embodies a method for decreasing the number of one or more types of hematopoietic progenitor cells, preferable CFU-GEMM cells, that comprises administering a therapeutically-effective amount of at least one LP82 antagonist, LP82 antisense polynucleotide fragment or LP82 antibody, as defined herein, to a cell, tissue, organ, mammal, human or patient in need of such therapy. It is contemplated that such method may further comprise administration of a therapeutically-effective amount of at least one additional hematopoietic cytokine antagonist, antisense polynucleotide fragment, or hematopoietic cytokine antibody.

It is further contemplated that the methods of the present invention may be administered prior to, simultaneously with, and/or subsequent to chemotherapy or radiation therapy as administered, for example, to a mammal, preferably a human, receiving treatment for cancer.

The present invention embodies a pharmaceutical composition comprising, alternatively consisting of or consisting essentially of, a hematopoietic progenitor cell-stimulating amount, or alternatively a CFU-GEMM cell-stimulating amount, or alternatively a lymphoid cell-stimulating amount, alternatively a therapeutically-effective amount of at least one LP82 polypeptide, LP82 polynucleotide, LP82 agonist, LP82 functional fragment and/or LP82 variant, as defined herein, and a pharmaceutically acceptable carrier, diluent or excipient. It is contemplated that such composition may further comprise a therapeutically effective amount of at least one additional-hematopoietic cytokine preferably Epo, TPO, IL-1, IL-3, IL-4, IL-5, IL-6, IL-7, IL-9, IL-11, G-CSF, GM-CSF, M-CSF and/or SCF, more preferably Epo, IL-3, SCF, G-CSF and/or GM-CSF, most preferably Epo, IL-3 and/or SCF.

The present invention further embodies a pharmaceutical composition comprising, alternatively consisting of or consisting essentially of, a hematopoietic progenitor cell-stimulating amount, or alternatively a CFU-GEMM cell-stimulating amount, or alternatively a therapeutically-effective amount of at least one LP82 antagonist, LP82 antisense polynucleotide fragment and/or LP82 antibody, as defined herein and a pharmaceutically acceptable carrier, diluent or excipient. It is contemplated that such composition may further comprise a therapeutically effective amount of at least one additional hematopoietic cytokine antagonist, hematopoietic cytokine antisense polynucleotide fragment or hematopoietic cytokine antibody.

DETAILED DESCRIPTION OF THE INVENTION

Figure 1:
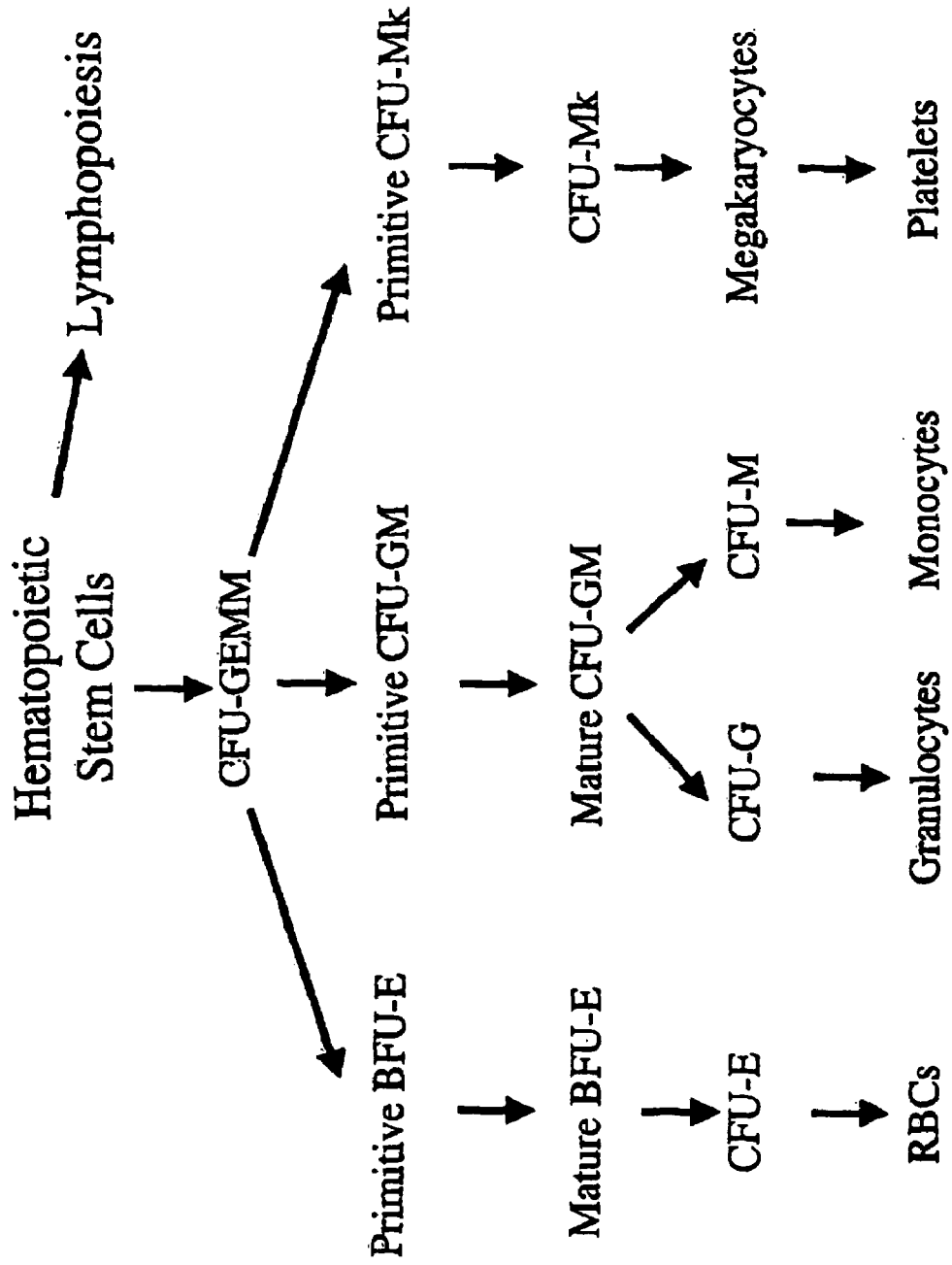
FIG. 1 provides a schematic of the cell lineages as they differentiate from a hematopoietic stem cell into the terminally differentiated RBCs, granulocytes, monocytes and platelets.

The invention is not limited to the particular embodiments described below, as variations of the particular embodiments may be made and still fall within the scope of the appended claims. The terminology used herein is for the purpose of describing particular embodiments, and is not intended to be limiting. Instead, the scope of the present invention will be established by the appended claims.

In this specification and the appended claims, the singular forms "a", "an", and "the" include plural reference unless the context clearly dictates otherwise.

Definitions

The term "amino acid" is used herein in its broadest sense, and includes naturally occurring amino acids as well as non-naturally occurring amino acids, including amino acid variants and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid variants and derivatives; naturally occurring non-proteogenic amino acids such as norleucine, β-alanine, ornithine, etc.; and chemically synthesized compounds having properties known in the art to be characteristic of amino acids.

The incorporation of non-natural amino acids, including synthetic non-native amino acids, substituted amino acids, or one or more D-amino acids into the LP82 polypeptides and/or fragments thereof and/or variants thereof of the present invention ("D- LP82 polypeptides") is advantageous in a number of different ways. D-amino acid-containing polypeptides exhibit increased stability in vitro or in vivo compared to L-amino acid-containing counterparts. Thus, the construction of LP82 polypeptides, incorporating D-amino acids can be particularly useful when greater stability is desired or required in vivo. More specifically, D-peptides are resistant to endogenous peptidases and proteases, thereby providing improved bioavailability of the molecule, and prolonged lifetimes in vivo when such properties are desirable. When it is desirable to allow a peptide to remain active for only a short period of time, the use of L-amino acids therein will permit endogenous peptidases, proteases, etc., to digest the molecule, thereby limiting the cell's exposure to the molecule. Additionally, D-peptides cannot be processed efficiently for major histocompatibility complex class II-restricted presentation to T helper cells, and are therefore less likely to induce humoral immune responses in the whole organism.

In addition to using D-amino acids, those of ordinary skill in the art are aware that modifications in the amino acid sequence of a LP82 polypeptide and/or any LP82 polypeptide variant can result in functional LP82 polypeptides that display equivalent or superior functional characteristics when compared to the original polypeptide sequence as shown in SEQ ID NO: 2, or any fragment thereof. Thus, the methods of the present invention contemplate alterations in the LP82 polypeptides and/or LP82 variants described herein that may include one or more amino acid insertions, deletions, substitutions, truncations, fusions, shuffling of subunit sequences, and the like, either from natural mutations or human manipulation, provided that the sequences produced by such modifications have substantially the same (or improved or reduced, as may be desirable) activity(ies) as the LP82 polypeptides and LP82 polypeptide variant thereof disclosed herein.

The term "LP82 antagonist" is used in the broadest sense and includes any molecule that partially or fully blocks, inhibits, or neutralizes a biological activity of a LP82 polypeptide as defined herein. In a similar manner, the term "LP82 agonist" is used in the broadest sense and includes any molecule that induces or increases the expression, stability, and/or biological activity of any LP82 polynucleotide or LP82 polypeptide. LP82 agonists and LP82 antagonists may include, for example, small molecules, LP82 polypeptides, LP82 polynucleotides, LP82 fragments as defined herein, and antibodies directed against a LP82 polypeptide. LP82 antagonists of the invention include, but are not limited to, nucleotide sequences, such as anti-sense and ribozyme molecules, and gene or regulatory sequence replacement constructs that can be used to inhibit expression of the LP82 gene. Suitable LP82 agonists include, but are not limited to, LP82 polypeptides, as well as fragments thereof, LP82 variants, and small organic molecules. Methods for identifying LP82 agonists or LP82 antagonists may comprise contacting an LP82 polypeptide with a candidate LP82 agonist or LP82 antagonist molecule and measuring a detectable change in one or more biological activities normally associated with the LP82 polypeptide.

"Antibodies" (Abs) and "immunoglobulins" (Igs) are glycoproteins having the same structural characteristics. While Abs exhibit binding specificity to a specific antigen, Igs include both Abs and other antibody-like molecules that lack antigen specificity. The term "antibody" is used in the broadest sense and specifically covers, without limitation, intact monoclonal antibodies, polyclonal antibodies, multi-specific antibodies (e.g., bispecific antibodies) formed from at least two intact antibodies, and antibody fragments so long as they exhibit the desired biological activity.

The term "fragment" or "fragment thereof" in reference to a LP82 gene or a DNA or cDNA sequence encoding LP82 or complementary sequence of such DNA or cDNA sequence, refers to a segment of an LP82 nucleic acid that comprises 15 or more nucleotides, preferably 30 or more nucleotides, even more preferably 50 or more nucleotides that are contiguous in the native nucleic acid molecule as shown in SEQ ID NO: 1 or its complementary sequence.

The term "fragment" or "fragment thereof" in reference to a LP82 polypeptide sequence, refers to a segment of an LP82 protein or polypeptide that comprises 15 or more amino acids, preferably 30 or more amino acids, even more preferably 50 or more amino acids that are contiguous in the native polypeptide as shown in SEQ ID NO: 2.

The term "functional" in reference to a LP82 polynucleotide, LP82 polypeptide, LP82 variant, and/or LP82 antibody is intended to mean that the particular molecule exhibits a biological activity, in vivo or in vitro, that is substantially similar or identical to a biological activity attributable to LP82 polypeptides as disclosed herein (e.g., the ability to induce the growth and/or differentiation of at least one type of hematopoietic progenitor cells, preferably CFU-GEMM cells).

"Functional fragment" as used herein, refers to an isolated segment of a LP82 polypeptide or variant thereof as defined herein or LP82 polynucleotide or complement thereof, that comprises a functionally distinct region such as an active site on an enzyme, a binding site for a LP82 agonist or antagonist, LP82 receptor, LP82 polypeptide, or LP82 antibody, or an LP82 antisense molecule. Functional fragments may be produced by means readily known to those in the art including, but not limited to, recombinant DNA methodologies, enzymatic/proteolytic digestions, or as natural products of alternative splicing processes.

The term "hematocrit" refers to a measurement of the ratio of the volume of red blood cells to the volume of whole blood cells as determined by an instrument used in determining the relative amounts of plasma and corpuscles in blood. The normal ranges for hematocrit are dependant on age and, after adolescence, the sex of the individual. It is understood that hematocrit targets will vary from one individual to another such that physician discretion may be appropriate in determining an actual target hematocrit for any given patient.

The term "LP82" refers to a nucleic acid, gene, cDNA (as shown in SEQ ID NO: 1), fragments thereof and sequence complementary to SEQ ID NO: 1 as well as to any polypeptide sequence (as shown in SEQ ID NO: 2) encoded thereby. The term "LP82" without further limitation also refers to both the native LP82 polypeptide (SEQ ID NO: 2) as well as the mature form of the LP82 polypeptide which is predicted to be amino acids 25 through 176 of the sequence shown in SEQ ID NO: 2. If not stated otherwise, the term "LP82 polypeptide" encompasses the full-length and functional fragments of the LP82 polypeptide as shown in SEQ ID NO: 2, as well as,, secreted, mature, fused, variant, alternatively spliced, and allelic forms thereof.

The term "LP82 composition" is intended to refer to a composition of matter comprising at least one LP82agonist, LP82 antagonist, LP82 polynucleotide, LP82 antisense polynucleotide, LP82 polypeptide, LP82 fragment, LP82 functional fragment, LP82 variant, LP82 fusion protein and/or LP82 antibody as defined herein.

An "LP82 polypeptide antibody" or "LP82 antibody" refers to an antibody as defined herein that recognizes and binds at least one epitope of a LP82 polypeptide as defined herein.

An "LP82 antisense polynucleotide" comprises at least 15 contiguous nucleotides of the complement of the sequence shown in SEQ ID NO: 1 that functions as an LP82 antagonist.

The term "LP82 variant" as used herein refers to a LP82 polynucleotide or LP82 polypeptide as shown in SEQ ID NOs: 1 or 2, respectively, as well any fragment thereof, that further comprises at least one of the various types of modifications contemplated herein. Furthermore, LP82 variant, as applied to a polypeptide, is intended to refer to a "functional" LP82 polypeptide, as defined herein, having at least about 95% amino acid sequence identity with an LP82 polypeptide having the deduced amino acid sequences as shown in SEQ ID NO: 2. Such LP82 polypeptide variants include, for instance, LP82 polypeptides wherein one or more amino acid residues are added, substituted or deleted, at the N- or C-terminus or within the sequence of SEQ ID NO: 2. Ordinarily, a LP82 polypeptide variant will have at least about 95% amino acid sequence identity, preferably at least about 96% amino acid sequence identity, yet more preferably at least about 97% amino acid sequence identity, yet more preferably at least about 98% amino acid sequence identity, yet more preferably at least about 99% amino acid sequence identity with the amino acid sequence as shown in SEQ ID NO: 2, with or without the signal peptide. Variants are contemplated to included allelic variants of LP82, i.e., encoded by the various alleles present in a population of mammals, preferably humans.

The term "half-life" as used herein refers to the time required for approximately half of the molecules making up a population of said molecules to be cleaved in vitro. More specifically, "plasma half-life" refers to the time required for approximately half of the molecules making up a population of said molecules to be removed from circulation or to be, otherwise, rendered inactive in vivo.

The term "hematopoietic cytokine" as used herein is a generic term that refers to any cytokine or factor that acts on a hematopoietic progenitor cell or is otherwise involved in the regulation of hematopoiesis, preferably it functions to induce proliferation and/or differentiation of a hematopoietic progenitor cell. Preferred hematopoietic cytokines include Epo, TPO, IL-1, IL-3,. IL-4, IL-5, IL-7, IL-9, IL-11, G-CSF, GM-CSF, M-CSF and SCF.

The term "hematopoietic progenitor cell" as used herein refers to any cell that is committed to a hematopoietic cell lineage but is not yet fully differentiated into a mature hematopoietic cell. Preferred hematopoietic progenitor cell types include CFU-GEMM, CFU-Mk, CFU-GM, BFU-E, megakaryocytes (see FIG. 1).

The term "mature hematopoietic cell" as used herein refers to a terminally differentiated hematopoietic cell, e.g., rbc, granulocyte, monocyte, platelet.

The term "isolated" when used in relation to a nucleic acid or protein, refers to a nucleic acid sequence or protein that is identified and separated from at least one contaminant with which it is ordinarily associated in its natural source. Isolated nucleic acid or protein is present in a form or setting that is different from that in which it is found in nature. In contrast, non-isolated nucleic acids or proteins are found in the state they exist in nature.

As used herein, the term "purified" or "to purify" means the result of any process which removes some contaminants from the component of interest, such as a protein or nucleic acid. The percent of a purified component is thereby increased in the sample.

The term "mature protein" or "mature polypeptide" as used herein refers to the form(s) of a protein produced by expression in a mammalian cell. It is generally hypothesized that once export of a growing protein chain across the rough endoplasmic reticulum has been initiated, proteins secreted by mammalian cells have a signal peptide (SP) sequence that is cleaved from the complete polypeptide to produce a "mature" form of the protein. Oftentimes, cleavage of a secreted protein is not uniform and may result in more than one species of mature protein. The cleavage site of a secreted protein is determined by the primary amino acid sequence of the complete protein and generally cannot be predicted with complete accuracy. Methods for predicting whether a protein has a SP sequence, as well as the cleavage point for that sequence, are available. A cleavage point may exist within the N-terminal domain of LP82 between amino acid 15 and amino acid 30, most preferably after amino acid 24 of the sequence shown in SEQ ID NO: 2. As one of ordinary skill would appreciate, cleavage sites sometimes vary from organism to organism and cannot be predicted with absolute certainty. Optimally, cleavage sites for a secreted protein are determined experimentally by amino-terminal sequencing of the one or more species of mature proteins found within a purified preparation of the protein.

The term "treatment" or "treating" as used herein describes the management and care of a patient for the purpose of combating or preventing a hematopoietic disease, condition, or disorder and includes the administration of a LP82 agonist, LP82 antagonist, LP82 polynucleotide, LP82 polypeptide, LP82 fragment, LP82 antisense polynucleotide, LP82 functional fragment, LP82 variant, LP82 antibody, and/or a LP82 composition to prevent the onset of the symptoms or complications, alleviate the symptoms or complications, or eliminate the disease, condition, or disorder.

A "therapeutically-effective amount" as used herein is the minimal amount of active agent (e.g., an LP82 polypeptide, a hematopoietic cytokine polypeptide, an LP82 antibody, a hematopoietic cytokine antibody) which is necessary to impart therapeutic benefit to a mammal. For example, a "therapeutically effective amount" to a mammal is such an amount which induces, ameliorates or otherwise causes an improvement in the pathological symptoms, disease progression or physiological conditions associated with or resistance to succumbing to a disorder.

The present invention demonstrates that LP82 activity is closely associated with hematopoietic processes. Applicants have shown that a LP82 polypeptide, both alone and when in combination with at least one other hematopoietic cytokine significantly increases the number of CFU-GEMM cells and increases the number of red blood cells, platelets, granulocytes and monocytes. LP82 polypeptide also increases the percentage of CFU-GEMM cells present in the S-phase of the cell cycle, i.e., LP82 increase CFU-GEMM cell-cycling status. Addition to human CD34+ cells of a LP82 polypeptide in combination with erythropoietin (Epo) and stem cell factor (SCF) and also in combination with Epo, SCF plus IL-3, significantly increased the number of CFU-GEMM hematopoietic progenitor cells when compared to control cells to which LP82 polypeptide was not added. CFU-GEMM differentiate ultimately into red blood cells, platelets, granulocytes and monocytes (FIG. 1). These colonies also contained increased numbers of megakaryocyte cells, demonstrating that LP82 affects a hematopoietic progenitor cell common to erythrocyte and megakaryocyte pathways. The applicants demonstrate that LP82 acts on a hematopoietic progenitor cell common to the erythrocyte, granulocyte/monocyte and megakaryocyte pathways to increase hematopoietic progenitor cells as well as mature hematopoietic cells. Further contemplated by the present invention is the ability of LP82 antagonists and antibodies to decrease the number of one or more types of hematopoietic progenitor cells as well as one or more types of mature hematopoietic cells.

Hematopoiesis

Hematopoiesis refers to the complex developmental process of the formation of new blood cells. In the hematopoietic system the only long-term self-renewing cells are the hematopoietic stem cells (HSC) from which all different types of blood cells are derived. HSC are lineage negative (Lin) for markers found on T cells, B cells, granulocytes, monocytes/macrophages, erythroid cells, etc. (for review see e.g., Weissman, et al., Annu. Rev. Cell Dev. Biol.

17:387–403, 2001). Human HSC are CD34$^+$, Thy-1$^+$, Lin$^-$, c-kit$^{lo}$, and CD38$^-$. HSC may differentiate into myeloid or lymphoid cells; each with their own specific cell-surface antigens (FIG. 1) The progenitor cells arising from hematopoietic stem cells are referred to as committed cells. The progenitor cells in the myeloid lineage, into which HSC differentiate, include colony-forming unit-granulocyte-erythrocyte-macrophage/monocyte-megakaryocyte ("CFU-GEMM"), blast-forming unit-erythroid ("BFU-E"), colony-forming unit-erythroid ("CFU-E"), colony-forming unit-granuloctye-macrophage ("CFU-GM"), colony-forming unit-granulocytic ("CFU-G"), colony-forming unit-macrophage ("CFU-M"), colony-forming unit-megakaryocytic ("CFU-MK"), and megakaryocytes. There is same variation in terminology in the art for these cells. Myeloid cells eventually give rise to terminally-differentiated platelets, granulocytes (neutrophils, eosinophils, basophils), monocytes, and erythrocytes. Myeloid cells eventually give rise to terminally-differentiated platelets, granulocytes (neutrophils, eosinophils, basophils), monocytes, and erythrocytes.

CFU-GEMM is the name of a pluripotent precursor cell type in the lineage of blood-forming cells which is capable of differentiating into all myeloid cell types. CFU-GEMM can be identified in a colony formation assay by the specific morphology of the cells. The cells may also be characterized by the cell-surface markers they express including CD33, CD34 and HLA-DR. It is CFU-GEMM cells upon which LP82 exerts its main activity leading to a significant increase in numbers of CFU-GEMM as evidenced both in vitro and in vivo in the examples herein. Some hematopoietic cytokines known to stimulate-CFU-GEMM include SCF, GM-CSF, IL-6, IL-3, IL-11 and Epo.

BFU-E (burst forming unit erythroid) are the earliest known erythroid precursor cells that eventually differentiate into erythrocyes, i.e., they are committed to the erythroid lineage. BFU-E produce large colonies of erythroid cells that consist of "bursts" of smaller colonies in a colony formation assay. Within the erythropoietic stem cell lineage, BFU-E precedes the more mature CFU-E. Maturation of the cells is accompanied by an increase in the number of Epo receptors on the cells. BFU-E respond to a large number of hematopoietic cytokines including IL3, EDF, IL4, IL6, IL9, IL1, SCF and Epo.

CFU-GM defines a pluripotent precursor cell type that is committed to differentiation into granulocytes and/or monocytes. CFU-GM can be identified morphologically in a colony formation assay by expression of the cell surface markers CD13, CD33, CD34 and HLA-DR. CFU-GM are stimulated by GM-CSF, SCF, IL-1, IL-4, and IL-6 among other hematopoietic cytokines. CFU-GM also responds to IL-9, IL-11, IL-12, Uteroferrin and bFGF.

As used herein, the term "CFU-GEMM stimulating amount" when referring to LP82 refers to an amount of LP82 that raises the baseline number of CFU-GEMM cells by at least 20%, preferably 30%, 40%, 50%, 60%, 70%, 80% or greater over the number of CFU-GEMM cells present in a mammal, human, or patient in the absence of LP82. As used herein, the term "hematopoietic progenitor stimulating amount" when referring to LP82 refers to an amount of LP82 that raises the baseline number of any hematopoietic progenitor cell type by at least 20%, preferably 30%, 40%, 50%, 60%, 70%, 80% or greater over the number of that type of hematopoietic progenitor cells present in a mammal, human, or patient in the absence of LP82. As used herein, the term "lymphoid cell stimulating amount" when referring to LP82 refers to an amount of LP82 that raises the baseline number of any type of lymphoid cell or lymphoid progenitor cell type by at least 20%, preferable 30%, 40%, 50%, 60%, 70%, 80% or greater over the number of that type of lymphoid cell or lymphoid progenitor cell present in a mammal, human, or patient in the absence of LP82.

A great number of blood-cell disorders are associated with low numbers of blood cells. They can be generally classified as anemia (low red blood cell count), leukopenia (low WBC count), neutropenia (low neutrophil count), thrombocytopenia (low platelet count) and pancytopenia (low RBC, WBC and platelets). Anemia occurs when the body is unable to produce enough red blood cells resulting in a decrease in the oxygen carrying capacity of the blood. It commonly occurs in patients with cancer and is also a common side effect of cancer treatment with chemotherapy and/or radiation therapy. Over 60% of patients treated with chemotherapy develop anemia. As demonstrated by the present invention, LP82 increases the number of CFU-GEMM cells which in turn ultimately increases the number of erythrocytes and may be useful for the treatment of anemia.

Thrombocytopenia is the presence of abnormally low levels of platelets in the circulating blood and is a common side effect of chemotherapy that results in the risk of bleeding. Cancer patients may also experience thrombocytopenia from other medications or as a consequence of their underlying cancer. Endogenous cytokines such as Epo, TPO, and SCF (among others) are typically upregulated following chemotherapy or radiation therapy as would be needed, for example, by a cancer patient receiving treatment for anemia or thrombocytopenia. Thus, LP82 polypeptides (and variants thereof) have the potential to act as a monotherapy for enhancing the recovery of platelets and/or erythrocytes following this type of therapy by increasing the number and/or cycling status of hematopoietic progenitor cells, particularly CFU-GEMM cells and cells which derive from CFU-GEMM cells.

Neutropenia is characterized by the presence of abnormally low levels of neutrophils in the circulating blood. Neutrophils are a type of white blood cell and one of the body's chief defense mechanisms to combat infection. The most common reason that cancer patients experience neutropenia is a side effect of chemotherapy.

Cytokines currently approved for use in the clinic to treat myelosuppression, a reduction in the ability of the bone marrow to produce blood cells, include G-CSF, EPO, IL-11 and GM-CSF; however, only EPO and G-CSF are widely used to treat anemia and neutropenia. Therefore, the present invention provides methods of treating or preventing hematopoietic disorders in mammals, preferably humans, or patients in need of such treatment comprising the administration of a therapeutically effective amount of a pharmaceutical composition comprising a LP82 polypeptide or variant thereof, optionally further comprising a therapeutically effective amount of one or more types of hematopoietic cytokines.

Treatment of Hematopoietic Disorders

The present invention provides methods of treating or preventing hematopoietic disorders in mammals, preferably humans, or patients in need of such treatment, comprising the administration of a therapeutically effective amount of at least one LP82 antagonist, LP82 agonist, LP82 polynucleotide, LP82 functional fragment, LP82 variant, LP82 antibody, and/or LP82 polypeptide, optionally in the presence of a therapeutically effective amount of at least one hematopoietic cytokine or hematopoietic cytokine antagonist or antibody. Such methods are particularly useful for enhancing or stimulating hematopoiesis, erythropoiesis, leukopoiesis, thrombocytopoiesis, production of neutrophils, monocytes, granulocytes, and/or platelets by stimulating the proliferation and/or differentiation of progenitors of such cells, as needed in various conditions and/or situations. Such conditions and situations include, but are not limited to, the following:

(a) inadequate platelet production, such as aplastic anemia, refractory anemias, leukemia, preleukemia/myelodysplastic syndromes, megaloblastic anemia, chemotherapy or radiation therapy, and existing platelet deficiency or an expected platelet deficiency (e.g., because of planned surgery including, but not limited to, organ/bone marrow transplantations);

(b) increased destruction of platelets, such as idiopathic thrombocytopenia purpura, other immune thrombocytopenias, HIV-associated thrombocytopenia, sepsis/disseminated intravascular coagulation, and vasculitis;

(c) abnormal platelet function, such as Glanzmann's thrombasthenia, acute/chronic leukemia, myeloproliferative disorders, uremia, platelet storage pool disease, Von Willebrand disease, and postoperative cardiovascular dysfunction, and (d) other blood coagulation disorders such as afibrinogenemia or wounds of any origin.

The generic term for platelet deficiency is thrombocytopenia, and hence the methods and compositions of the present invention are generally available for treating thrombocytopenias. Thrombocytopenias may be present for various reasons, including chemotherapy, radiation therapy, surgery, accidental blood loss, and other specific disease conditions. Exemplary specific disease conditions that involve thrombocytopenia and may be treated in accordance with this invention are: aplastic anemia, idiopathic thrombocytopenia, and certain metastatic tumors which result in thrombocytopenia. Also, certain treatments for Acquired Immunodeficiency Syndrome (AIDS) result in thrombocytopenia (e.g., AZT). Certain wound healing disorders might also benefit from an increase in platelet numbers.

With regard to anticipated platelet deficiencies, e.g., due to future surgery, the LP82 polypeptide, LP82 agonist or variants thereof could be administered several days to several hours prior to the need for platelets. With regard to acute situations, e.g., accidental and massive blood loss, the LP82 polypeptide, agonist, and/or variants thereof could be administered along with blood or purified platelets.

Furthermore, the present invention provides LP82 agonists, LP82 antagonists, LP82 polynucleotides, LP82 polypeptides, LP82 functional fragments, LP82 variants, LP82 antibodies, and LP82 compositions that modulate intracellular signaling pathways dependent on at least one hematopoietic, erythropoietic, leukopoietic or thrombopoietic related function.

LP82 polypeptides can potentiate or stimulate T-cell activation and/or proliferation and, thereby, have therapeutic utility for treating infections caused by viruses including, but not limited to, HIV, immunocompromised disorders, and for treating various autoimmune diseases including, but not limited to, rheumatoid arthritis, lupus, graft-versus-host, host-versus-graft, insulin-dependent diabetes, autoimmune encephlomyelitis, and multiple sclerosis.

A preferred embodiment of the present invention provides methods of treating or preventing hematopoietic disorders including, but not limited to, anemia and disorders commonly associated with anemia, comprising the administration to a mammal in need of such treatment a therapeutically effective amount of LP82 polypeptide having the sequence as shown in SEQ ID NOs: 2–3 or a variant thereof, optionally also administering to the mammal a therapeutically effective amount of a hematopoietic cytokine.

A preferred embodiment of the present invention provides a method of treating or preventing hematopoietic disorders including, but not limited to, erythrocytosis, and leukemia comprising the administration of a therapeutically effective amount of a LP82 antagonist to a mammal in need of such treatment, optionally also administering to the mammal a therapeutically effective amount of a hematopoietic cytokine antagonist or hematopoietic cytokine antibody.

The present invention further provides a pharmaceutical composition that comprises at least one LP82 agonist, LP82 antagonist, LP82 polynucleotide, LP82 polypeptide, LP82 functional fragment, LP82 variant, LP82 antibody, and/or LP82 composition together with one or more pharmaceutically acceptable diluents, carriers, or excipients therefor. Also contemplated are such compositions further comprising a hematopoietic cytokine.

The present invention also provides a method of treating or preventing hematopoietic disorders including, but not limited to, anemia and/or disorders commonly associated with anemia, comprising the administration to a mammal in need thereof of a therapeutically effective amount of a LP82 composition wherein said composition has at least one activity, such as, but not limited to, inducing differentiation and/or proliferation of erythroid, CFU-GM and/or megakaryocyte progenitor cells. An LP82 polypeptide can thus be screened for a corresponding activity according to these effects.

The invention further provides for the use of a LP82 agonist, LP82 antagonist, LP82 nucleic acid, LP82 polypeptide, LP82 functional fragment, LP82 variant, and/or LP82 antibody in the manufacture of a medicament for the treatment or prevention of anemia, and disorders associated with such conditions.

The novel methods contemplated by the present invention include methods of using LP82 polynucleotides and LP82 polypeptides as shown in SEQ ID NOS: 1 and 2, respectively, and functional fragments thereof, as well as LP82 polynucleotide variants and/or LP82 polypeptide variants that further comprise one or more substitutions, deletions, insertions, inversions, additions, or changes in glycosylation sites or patterns yet have substantially similar biological activities and/or pharmaceutically desired properties as the corresponding unmodified LP82 polynucleotide or LP82 polypeptide to treat mammals, preferably humans, to alter the hematopoietic cell composition of those in need of such treatment.

LP82 Polypeptide Variants

LP82 polypeptides effective in the present invention are contemplated to comprise variants of about 95% or greater, preferably 96% or greater, even more preferably 97%, 98%, or 99% or more sequence identity with the sequence shown in SEQ ID NO: 2. In one embodiment of the present invention, a single amino acid change is made within the LP82 polypeptide which has the amino acid sequence as shown in SEQ ID NO: 2. Alternatively, two, three, four, five, six, seven, or eight changes are made within the LP82 polypeptide sequence as shown in SEQ ID NO: 2 amino acids about 1 to about 176 or amino acids about 25 to about 176. An amino acid change may be an insertion, substitution and/or deletions. The changes may be contiguous, independent, or a combination of both. The changes may be at the N- and/or C-terminus and/or internally located. Most preferably the LP82 polypeptide used in the methods and compositions of the invention has 0 or 1 amino acid changes from the sequence shown in SEQ ID NOs: 2 or 3.

As the skilled artisan understands, many substitutions, and/or other changes to a protein's sequence or structure, can be made to a polypeptide without substantially affecting its biological activity or characteristics. For example, making conservative amino acid substitutions, or changing one amino acid for another from the same class of amino acids, (e.g., negatively charged residues, positively charged residues, polar uncharged residues, and non-polar residues, or any other classification acceptable in the art) are often made without significant effects upon function. Modifications of the LP82 polypeptide sequence as shown in SEQ ID NO: 2 made in accordance with Table 1 herein are expected to result in LP82 variants that retain the same or substantially similar biological activity as the unmodified LP82 polypeptide based on art-recognized substitutability of certain amino acids (see, e.g., M. Dayhoff, *In Atlas of Protein Sequence and Structure*, Vol. 5, Supp. 3, pgs 345–352, 1978) and are also contemplated as being useful in the methods of the present invention.

Allelic variants of the DNA sequence shown in SEQ ID NO: 1, including those containing silent mutations and those in which mutations result in amino acid sequence changes, are contemplated to fall within the scope of the methods and compositions of the present invention, as are proteins which are allelic variants of SEQ ID NO: 2. Allelic variants of SEQ ID NO: 2 can be cloned by probing cDNA or genomic libraries from different individuals or tissues according to standard procedures known in the art. Exemplary allelic variants are described in international patent application WO 99/27103 and also shown in SEQ ID NO: 3 herein.

TABLE 1

| ORIGINAL RESIDUE | EXEMPLARY SUBSTITUTIONS |
| --- | --- |
| ALA | SER, THR |
| ARG | LYS |
| ASN | HIS, SER |
| ASP | GLU, ASN |
| CYS | SER |
| GLN | ASN, HIS |
| GLU | ASP, GLU |
| GLY | ALA, SER |
| HIS | ASN, GLN |
| ILE | LEU, VAL, THR |
| LEU | ILE, VAL |
| LYS | ARG, GLN, GLU, THR |
| MET | LEU, ILE, VAL |
| PHE | LEU, TYR |
| SER | THR, ALA, ASN |
| THR | SER, ALA |
| TRP | ARG, SER |
| TYR | PHE |
| VAL | ILE, LEU, ALA |
| PRO | ALA |

One factor that can be considered in making amino acid changes in an LP82 variant polypeptide is the hydropathic index of amino acids. The importance of the hydropathic amino acid index in conferring interactive biological function on a protein has been discussed by Kyte and Doolittle (*J. Mol. Biol.*, 157:105–132, 1982). It is accepted that the relative hydropathic character of amino acids contributes to the secondary structure of the resultant protein. This, in turn, affects the interaction of the protein with molecules such as enzymes, substrates, receptors, ligands, DNA, antibodies, antigens, etc. Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide, polypeptide, or protein can be substituted for other amino acids having a similar hydropathic index or score and produce a resultant peptide, etc., having similar biological activity, i.e., which still retains biological functionality. In making such changes, it is preferable that amino acids having hydropathic indices within ±2 are substituted for one another. More preferred substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant peptide, etc., having similar biological activity, i.e., still retaining correct biological function. In making such changes, amino acids having hydropathic indices within ±2 are preferably substituted for one another, those within ±1 are more preferred, and those within ±0.5 are most preferred.

As outlined above, amino acid substitutions in a LP82 polypeptide can be based on the relative similarity of the amino acid side-chain substituents, for example, their hydrophobicity, hydrophilicity, charge, size, etc. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine.

LP82 polypeptide variants having biological activities, in vivo or in vitro, that are similar or identical to those described herein, for example, the ability to increase the number of CFU-GEMM cells or to induce or enhance differentiation and/or proliferation of erythroid and/or megakaryocyte progenitor cells are also useful in the methods of the present invention and as such are contemplated by the present invention. LP82 variant polypeptides, while functionally related, by definition include amino acid sequences that differ in one or more positions up to about 10 positions from the sequence as shown in SEQ ID NO: 2. LP82 variant polypeptides that are useful in the methods of the present invention can be generated by deletion, insertion, inversion, and/or substitution of one or more amino acid residues in said LP82 polypeptide with the sequence of SEQ ID NO: 2. Such LP82 variants can generally be made by solid phase or recombinant techniques in which, for example, single or multiple conservative amino acid substitutions are made, according to Table 1.

Generally, in the case of multiple substitutions, it is preferred that between 95% to 99% of the residues of a LP82 polypeptide variant are identical to the corresponding sequence as shown in SEQ ID NO: 2; it is more preferable that between 96% to 99% of the residues of a LP82 polypeptide variant are identical to the corresponding contiguous sequence as shown in SEQ ID NO: 2; most preferably between 97% to 99% of the residues of a LP82 variant are identical to the corresponding contiguous sequence as shown in SEQ ID NO: 2. Examples of preferred LP82 variants include the LP82 polypeptide variants as shown in SEQ ID NO: 3. Percent sequence identity is determined by conventional methods, see for example Altschul et al., *Bull. Math. Bio.* 48:603–616 (1986) and Henikoff and Henikoff, *PNAS USA* 89:10915–10919 (1992).

Another class of LP82 variant that would be useful in the methods of the present invention includes LP82 polypeptides as defined herein further comprising one or more amino acid substitutions that result in an altered glycosylation pattern as compared to the corresponding unsubstituted LP82 polypeptide.

The term "N-glycosylated polypeptide" refers to polypeptides having one or more NXS/T motifs in which the nitrogen atom in the side chain amide of the asparagine is covalently bonded to a glycosyl group. "X" refers to any naturally occurring amino acid residue except proline. The "naturally occurring amino acids" are glycine, alanine, valine, leucine, isoleucine, proline, serine, threonine, cysteine, methionine, lysine, arganine, glutamic acid, asparatic acid, glutamine, asparagine, phenylalanine, histidine, tyrosine and tryptophan. N-glycosylated proteins are optionally O-glycosylation.

The term "O-glycosylated polypeptide" refers to polypeptides having one or more serines and/or threonine in which the oxygen atom in the side chain is covalently bonded to a glycosyl group. O-Glycosylated proteins are optionally N-glycosylation. Glycosylated polypeptides can be prepared recombinantly by expressing a gene encoding a polypeptide in a suitable mammalian host cell, resulting in glycosylation of side chain amides found in accessible NXT/S motifs on the polypeptide surface and/or of side chain alcohols of surface accessible serines and threonines. Specific procedures for recombinantly expressing genes in mammalian cells are provided hereinbelow. Other procedures for preparing glycosylated proteins are disclosed in EP 640,619, the entire teachings of which are incorporated herein by reference. Unglycosylated polypeptides can be prepared recombinantly by expressing a gene encoding a polypeptide in a suitable prokaryotic host cell. The LP82 polypeptides and LP82 variants of the present invention can also be glycosylated or unglycosylated. A glycosylated polypeptide is modified with one or more monosaccharides or oligosaccharides. A monosaccharide is a chiral polyhydroxyalkanol or polyhydroxyalkanone which typically exists in hemiacetal form. An "oligosaccharide" is a polymer of from about 2 to about 18 monosaccharides which are generally linked by acetal bonds. One type of glycosyl group commonly found in glycosylated proteins is N-acetylneuraminic acid. A glycosylated polypeptide can be N-glycosylated and/or O-glycosylated, preferably N-glycosylated.

Another class of LP82 variant that may be useful in the methods of the present invention includes LP82 polypeptides as defined herein further comprising at least one oligopeptide or amino acid added onto the N-terminus and/or C-terminus. An "oligopeptide" is a chain of from two to about twenty-five amino acids connected at their N- and C-termini by peptide bonds. Suitable oligopeptides and amino acids are those that do not significantly decrease the biological activity of the LP82 polypeptide as defined herein and do not substantially detract from the desired pharmaceutical and pharmacological properties of the LP82 polypeptide. A preferred example of such a modification includes a LP82 polypeptide as defined herein further comprising a leader sequences found in other polypeptides, such as pretrypsinogen leader sequence.

The LP82 variants useful in the methods of the present invention also include LP82 polypeptides as defined herein further comprising one or more polyethylene glycol groups (hereinafter "PEG" groups). The PEG groups can be bonded to the N-terminus or to amine groups or thiol groups in the amino acid side chain(s) of LP82 polypeptides. Suitable PEG groups generally have a molecular weight between about 5,000 and 40,000 atomic mass units. Procedures for preparing PEGylated polypeptides are disclosed in Mumtaz and Bachhawat, *Indian Journal of Biochemistry and Biophysics* 28:346, 1991, and Francis et al., *International Journal of Hematology* 68:1, 1998.

The LP82 polypeptides as defined herein can also be expressed and used in a modified form, such as a fusion protein or a "tagged" protein. LP82 fusion proteins represent a hybrid protein molecule not found in nature comprising a translational fusion or enzymatic fusion in which two or more different proteins, fragments, or variants thereof are covalently linked on a single polypeptide chain. The two or more proteins may optionally be separated by a linker sequence to allow for independent activity of each of the fused proteins. Human serum albumin, the C-terminal domain of thrombopoietin, the C-terminal extension peptide of hCG, and/or a Fc fragment are examples of proteins which could be fused with LP82 polypeptides, LP82 fragments and/or LP82 variants for use in the present invention. As used herein, "Fc fragment" of an antibody has the meaning commonly given to the term in the field of immunology. Specifically, this term refers to an antibody fragment which binds complement and is obtained by removing the two antigen binding regions (the Fab Fragments) from the antibody. Thus, the Fc fragment is formed from approximately equal sized fragments from both heavy chains, which associate through non-covalent interactions and disulfide bonds. The Fc Fragment includes the hinge regions and extends through the $C_H2$ and $C_H3$ domains to the C-terminus of the antibody. Procedures for preparing fusion proteins are disclosed in EP 394827, Tranecker et al., *Nature* 331:84, 1988, and Fares, et al., *Proc. Natl. Acad. Sci. USA* 89:4304, 1992.

Many fusion proteins can be secreted by virtue of heterologous secretion signals in regions that can be removed prior to final preparation of the polypeptide. Such methodologies are well known in the art. In a preferred process for protein expression and subsequent purification, the LP82 gene can be modified at the 5' end to incorporate several histidine residues at the amino terminus of the LP82 protein resulting from its expression. This "histidine tag" enables a single-step protein purification method referred to as "immobilized metal ion affinity chromatography" (IMAC), essentially as described in U.S. Pat. No. 4,569,794, which is incorporated herein by reference. The IMAC method enables rapid isolation of substantially pure recombinant LP82 protein starting from a crude extract of cells that express a modified recombinant protein, as described above.

A LP82 polypeptide variant useful in the present invention as well as the nucleic acid encoding it may also be defined with reference to a percent identity similarity to either SEQ ID NO: 2 or SEQ ID NO: 1. Sequence identity refers to a comparison between two molecules using standard algorithms well known in the art. Although any suitable sequence comparison algorithm can be used for this purpose, for illustration, this embodiment shall be described with reference to the well-known Smith-Waterman algorithm using SEQ ID NO: 2 as the reference sequence to define percent identity to a comparator sequence. When sequence identity is used with reference to a polypeptide, either the entire polypeptide may be used in the comparison or instead only a defined sub-region thereof.

The choice of parameter values for matches, mismatches, and inserts or deletions is arbitrary. A preferred set of values for use with the Smith-Waterman algorithm is set forth in the "maximum similarity segments" approach, which uses values of 1 for a matched residue, and −1/3 for a mismatched residue (see, Waterman, *Bulletin of Mathematical Biology*, 46, 473–500, 1984). Insertions and deletions (indels), x, are weighted as follows:

$X_k = 1 + k/3$ where k is the number of residues in a given insert or deletion. For example, a comparator sequence that has 20 substitutions and 3 insertions relative to the 250 residue reference protein sequence would have an identity of:

[(1×250)−(1/3×20)−(1+3/3)]/250=96% identical.

Since LP82 variants can be produced easily by conventional recombinant or solid phase synthetic techniques known in the art, the methods of the present invention contemplates the use of LP82 polynucleotide and LP82 polypeptide variants in the methods of the present invention to the extent that such variants have at least 70% and 80% identity to a contiguous sequence of nucleotides or amino acids as shown in SEQ ID NO: 1 or 2, respectively, while retaining substantially similar activity as the corresponding LP82 polynucleotide or LP82 polypeptide.

LP82 Polypeptide Synthesis

Functional fragments of LP82 polypeptides and LP82 variants may be generated by any number of suitable techniques, including chemical synthesis of any portion of SEQ ID NO: 2, proteolytic digestion of LP82 polypeptides or LP82 variants, or most preferably, by recombinant DNA mutagenesis techniques well known to the skilled artisan. For example, in a preferred method, a nested set of deletion mutations are introduced into a nucleic acid sequence encoding a LP82 polypeptide such that varying amounts of the protein coding region are deleted, either from the amino terminal end or from the carboxyl end of the protein molecule. This method can also be used to create internal fragments of the intact protein in which both the carboxyl and amino terminal ends are removed.

Functional fragments of the proteins disclosed herein may be produced as described above, preferably using cloning techniques to engineer smaller versions of the intact gene, deleting sequence from the 5' end, the 3' end, from both ends, or from an internal site. Fragments may be tested for biological activity using any suitable assay, for example, the ability to induce and/or enhance differentiation and/or proliferation of hematopoietic progenitor cells, e.g., erythroid, megakaryocyte or CFU-GM or CFU-GEMM progenitor cells in vivo or in vitro.

Those skilled in the art will recognize that the LP82 gene could be obtained by a plurality of recombinant DNA techniques including, for example, as described in international application WO 99/27103, incorporated herein.

Skilled artisans will recognize that the proteins used in the present invention can be synthesized by a number of different methods, such as chemical methods well known in the art, including solid phase peptide synthesis or recombinant methods. Both methods are described in U.S. Pat. No. 4,617,149, incorporated herein by reference. The proteins useful in the present invention can also be produced by recombinant DNA methods using the cloned LP82 gene. Recombinant methods are preferred if a high yield is desired. Expression of the cloned gene can be carried out in a variety of suitable host cells, well known to those skilled in the art. For this purpose, the LP82 gene is introduced into a host cell (e.g., prokaryote, mammalian, yeast, SF9) by any suitable means, well known to those skilled in the art. The recombinantly-produced protein may be purified from cellular extracts of transformed cells by means known well in the art.

The LP82 polypeptides used in the methods of the present invention may be synthesized either by direct expression or as a fusion protein comprising the LP82 polypeptide of interest as a translational fusion with another protein or peptide which optionally may be removable by enzymatic or chemical cleavage. It is often observed in the production of certain peptides in recombinant systems that expression as a fusion protein prolongs the life span, increases the yield of the desired peptide, provides a convenient means of purifying the protein. This is particularly relevant when expressing mammalian proteins in prokaryotic hosts. A variety of peptidases which cleave a polypeptide at specific sites or digest the peptides from the amino- or carboxy-termini of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites (See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990)).

LP82 Antibodies

The methods of the present invention may also utilize LP82 antibodies. Exemplary antibodies include polyclonal, monoclonal, humanized, bispecific, and heteroconjugate antibodies.

Methods for preparing polyclonal and monoclonal antibodies are well known in the art (see for example, Sambrook et al., *Molecular Cloning: A Laboratory Manual, Second Edition* (Cold Spring Harbor, N.Y., 1989); and Hurrell, J. G. R., Ed., *Monoclonal Hybridoma Antibodies: Techniques and Applications* (CRC Press, Inc., Boca Raton, Fla., 1982). Monoclonal antibodies may also be made by recombinant DNA methods, such as those described in U.S. Pat. No. 4,816,567, incorporated herein.

As would be evident to one of ordinary skill in the art, polyclonal antibodies can be generated from numerous animals such as goats, sheep, rabbits, mice, rats, chickens. The immunogenicity of an LP82 polypeptide may be increased through the use of an adjuvant. Exemplary assays for detecting antibodies specific to a polypeptide of interest are described in detail in *Antibodies: A Laboratory Manual*, Harlow and Lane (Eds.), Cold Spring Harbor Laboratory Press, 1988.

LP82 antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

The LP82 antibodies used in the methods of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary-determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody optimally also will comprise at least a portion of an immunoglobulin constant region (Fc), typically that of a human immunoglobulin [Jones, et al., *Nature* 321: 522–5, 1986; Riechmann, et al., *Nature* 332:323–7, 1988; and Presta, Curr. Op. Struct. Biol. 2:593–6, 1992.

Methods for humanizing non-human antibodies are well known in the art. Humanization can be essentially performed following the method as described in Jones, et al., *Nature* 321: 522–5, 1986; Riechmann, et al., *Nature* 332: 323–7, 1988; Verhoeyen, et al., *Science* 239(4847): 1534–6, 1988, by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. Human LP82 antibodies can also be produced using various techniques known in the art, including phage display libraries (Hoogenboom and Winter, *J. Mol. Biol.* 227: 381–8, 1992; Marks, et al., *J. Mol. Biol.* 222: 581–97, 1991). The techniques of Cole, et al., and Boerner, et al., are also available for the preparation of human monoclonal antibodies (Cole, et al., *Monoclonal Antibodies and Cancer Therapy*, Alan R. Liss, p. 77 (1985) and Boerner, et al., *J. Immunol.* 147: 86–95, 1991). Similarly, human LP82 antibodies can be made by introducing human immunoglobulin loci into transgenic animals, e.g., mice in which the endogenous immunoglobulin genes have been partially or complete inactivated. Upon challenge, human LP82 polypeptide antibody production is observed, which closely resembles that seen in humans in all respects, including gene rearrangement, assembly and antibody repertoire. This approach is described., for example, in U.S. Pat. Nos. 5,545,807; 5,545,806; 5,569,825; 5,625,126; 5,633,425; 5,661,016.

Bi-specific antibodies are monoclonal, preferably human or humanized, antibodies that have binding specificities for at least two different antigens. In the present case, one of the binding specificities may be for an LP82 polypeptide, the other one is for any other antigen, and preferably for a cell-surface protein or receptor or receptor subunit. Methods for making bispecific antibodies are known in the art. Antibodies with more than two valencies are contemplated. For example, trispecific antibodies can be prepared (Tutt, et al., *J. Immunol.* 147: 60–9, 1991).

The use of heteroconjugated antibodies is also contemplated as part of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/20373]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The usefulness of a LP82 agonist, LP82 antagonist, LP82 polynucleotide, LP82 polypeptide, LP82 variant, LP82 antibody, and/or a LP82 composition for the methods of the present invention can be determined by one skilled in the art without undue experimentation by application of the methods or assays described herein or otherwise known in the art. A LP82 agonist, LP82 antagonist, LP82 polynucleotide, LP82 polypeptide, LP82 variant, LP82 antibody, and/or LP82 composition can be tested for biological activity or functionality as described herein, or as otherwise known in the art (see, e.g., Xunxiang Du and David A. Williams, Blood, 89(11), (1997); and, Donald Metcalf and Nicos A. Nicola, The Hemopoietic Colony-Stimulating Factors (1995)). Similarly, the usefulness of a LP82 agonist, LP82 antagonist, LP82 polynucleotide, LP82 polypeptide, LP82 variant, LP82 antibody, and/or a LP82 composition in the methods of the present invention can be assessed or quantified using the in vitro models or in vivo models of hematopoiesis as described herein (see Examples) or assays otherwise known in the art.

The present invention still further relates to methods for identifying compounds which modulate the expression of the mammalian LP82 gene and/or the synthesis or activity of mammalian LP82 gene products. Such compounds include therapeutic compounds that can be used as pharmaceutical compositions to reduce or eliminate the symptoms of mammalian hematopoietic disorders such as anemia. Cellular and non-cellular assays are described that can be used to identify compounds that interact with the LP82 gene and/or gene product, e.g., modulate the activity of the LP82 gene and/or bind to the LP82 gene product. Such cell-based assays of the invention utilize cells, cell lines, or engineered cells or cell lines that express the LP82 gene product.

First, cell-based systems can be used to identify compounds that may act to ameliorate hematopoietic disorder symptoms. Such cell systems can include, for example, recombinant or non-recombinant cells, such as cell lines, that express the LP82 gene. In utilizing such cell systems, cells that express LP82 may be exposed to a compound suspected of exhibiting an ability to ameliorate hematopoietic disorder symptoms, at a sufficient concentration and for a sufficient time to elicit such an amelioration of such symptoms in the exposed cells. After exposure the cells can be assayed to measure alterations in the expression of the LP82 gene, e.g., by assaying cell lysates for LP82 mRNA transcripts (e.g., by Northern analysis) or for LP82 gene products expressed by the cell. Compounds that modulate expression of the LP82 gene are good candidates as therapeutics.

In addition, animal-based systems or models for a mammalian hematopoietic disorder, for example, transgenic mice containing a human or altered form of LP82 gene, may be used to identify capable of ameliorating symptoms of the disorder. Such animal models may be used as test substrates for the identification of drugs, pharmaceuticals, therapies and interventions. For example, animal models may be exposed to a compound suspected of exhibiting an ability to ameliorate symptoms, at a sufficient concentration and for a sufficient time to elicit such an amelioration of the symptoms of the hematopoietic disorder. An animal's response to a particular treatment may be monitored by assessing reductions in the symptoms attributable to the disorder. Treatments that favorably affect hematopoietic disorder-like symptoms may be considered as candidates for human therapeutic intervention in such a disorder. Dosages of test agents may be determined by deriving dose-response curves In one embodiment, methods of the present invention comprise contacting a compound to a cell, measuring the level of LP82 gene expression, gene product expression, or gene product activity, and comparing the level to the level of LP82 gene expression, gene product expression, or gene product activity produced by the cell in the absence of the compound. If the level obtained in the presence of the compound differs from that obtained in its absence, a compound that modulates the expression of the mammalian LP82 gene and/or the synthesis or activity of mammalian LP82 gene products has been identified.

In an alternative embodiment, methods of the present invention comprise administering a compound to a host, (e.g., a wild-type or transgenic animal that expresses a LP82 transgene or a LP82 variant transgene) and measuring the level of LP82 gene expression, gene product expression, or gene product activity. The measured level is compared to the level of LP82 gene expression, gene product expression, or gene product activity in a host that is not exposed to the compound. If the level obtained when the host is exposed to the compound differs from that obtained when the host is not exposed to the compound, a compound that modulates either the expression of the mammalian LP82 gene, the synthesis or activity of the LP82 gene product, the compound may be used in the methods of the present invention.

Methods of the present invention can comprise, for example administering compounds which modulate the expression of a mammalian LP82 gene and/or the synthesis and/or the activity of a mammalian LP82 gene product, so that symptoms of a hematopoietic disorder are ameliorated. Alternatively, in those instances whereby the mammalian hematopoietic disorder results from LP82 gene mutations, such methods can comprise supplying the mammal with a nucleic acid molecule encoding an unimpaired LP82 gene product such that an unimpaired LP82 gene product is expressed and symptoms of the disorder are ameliorated.

Another embodiment of the present invention includes a method for the treatment of mammalian hematopoietic disorder comprising the administration of a cell comprising a nucleic acid molecule that encodes an unimpaired LP82 gene product to mammal in need of such treatment such that the cell expresses an unimpaired LP82 gene product and/or polypeptide encoded thereby, and symptoms of the disorder are ameliorated.

Polynucleotide Inhibition of LP82

Alternatively, symptoms of certain hematopoietic disorders such as, erythrocytosis which involve a higher than normal number of red cells, may be ameliorated by inhibiting the level of LP82 gene expression and/or LP82 gene product activity. Methods for inhibiting or reducing the level of LP82 gene product synthesis or expression can include, for example, methods such as inhibitory antisense, ribozyme and triple helix approaches. In another embodiment, symptoms of hematopoietic disorders may be ameliorated by decreasing the level of LP82 gene expression and/or LP82 gene product activity by using LP82 gene sequences in conjunction with well-known antisense, gene "knock-out", ribozyme, and/or triple helix methods to decrease the level of LP82 gene expression. Among the compounds that may exhibit the ability to modulate the activity, expression or synthesis of the LP82 gene, including the ability to ameliorate the symptoms of a mammalian hematopoietic disorder, are antisense, ribozyme, and triple helix molecules. Such molecules may be designed to reduce or inhibit either an unimpaired, or if appropriate, a mutant target gene and/or aberrant LP82 activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be) One skilled in the art can ascertain a tolerable degree of mismatch by use of standard procedures to determine the melting point of the hybridized complex.

In one embodiment, oligonucleotides complementary to non-coding regions of the LP82 gene could be used in an antisense approach to inhibit translation of endogenous LP82 mRNA. Antisense nucleic acids should be at least six nucleotides in length, and are preferably oligonucleotides ranging from 6 to about 50 nucleotides in length. In specific aspects the oligonucleotide is at least nucleotides, at least 17 nucleotides, at least 25 nucleotides or at least 50 nucleotides. Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence. The oligonucleotides can be DNA or RNA or chimeric mixtures or derivatives or modified versions,thereof, single- stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, *Proc. Natl. Acad. Sci. U.S.A.* 86, 6553–6556; Lemaitre, et al., 1987, *Proc. Natl. Acad. Sci. U.S.A.* 84:648; PCT Publication No. W088/09810, published Dec. 15, 1988) or the blood-brain barrier (see, e.g., PCT Publication No. W089/10134, published Apr. 25, 1988), hybridization-triggered cleavage agents (see, e.g., Krol et al., 1988, *BioTechniques* 6:958) or intercalating agents (see, e.g.. Zon, 1988, *Pharm. Res.* 5: 539). To this end, the oligonucleotide may be conjugated to another molecule, e.g., a peptide, hybridization triggered cross-linking agent, transport agent, hybridization-triggered cleavage agent, etc. The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D- is galactosylqueosine, inosine, NG-isopentenyladenine, 1-methylguanine, 1-methylinosine, 2,2-dimethyl guanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid -methylester, uracil-5-oxyacetic acid (v), 5-methyl-2-thiouracil, 3-(3-amino-3-N-2-carboxypropyl) uracil, and 2,6-diaminopurine. The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which the strands run parallel to each other (Gautier, et al., 1987, *Nucl. Acids Res.* 15:6625). The oligonucleotide is a 2'-O-methylribonucleotide (Inoue, et al., 1987, *Nucl. Acids Res.* 15, 6131), or a chimeric RNA-DNA analogue (Inoue, et al., 1987, *FEBS Lett.* 215:327). Oligonucleotides of the invention may he synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, *Nucl. Acids Res.* 16:3209). Methyl-phosphonate oligonucleotides can be prepared by use of controlled pore glass polymer supports (Sarin, et al., 1988, *Proc. Natl. Acad. Sci. U.S.A.* 85:7448). While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells (e.g., antisense molecules can be injected directly into the tissue site) or modified antisense molecules, designed to target the desired cells (e.g., antisense linked to peptides or antibodies that specifically bind receptors or antigens expressed on the target cell surface), can be administered systemically. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect targeT-cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art and can be plasmid, viral, or others known in the art, used for replication and expression in mammalian cells.

Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304), the promoter contained in the 3' long terminal repeat of Rous sarcoma virus (Yamamoto, et al., 1980, *Cell* 22:787), the herpes thymidine kinase promoter (Wagner, et al., 1961, *Proc. Natl. Acad. Sci. U.S.A.* 78:1441), the regulatory sequences of the metallothionein gene (Brinster, et al., 1982, *Nature* 296:39), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically). Ribozyme molecules designed to catalytically cleave target gene mRNA transcripts can also be used to prevent translation of target gene mRNA and, therefore, expression of target gene product. (see, e.g., PCT International Publication W090/11364, published Oct. 4, 1990; Sarver, et al., 1990, *Science* 247:1222).

Ribozymes are enzymatic RNA molecules capable of catalyzing the specific cleavage of RNA. (For review, see Rossi, 1994, *Current Biology* 4:469). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage (For this sequence, see, e.g., U.S. Pat. No. 5,093,246, which is incorporated herein by reference in its entirety). While ribozymes that cleave mRNA at site specific recognition sequences can be used to destroy target gene mRNAs, the use of hammerhead ribozymes is preferred. Hammerhead ribozymes cleave mRNAs at locations dictated by 2S flanking regions that form complementary base pairs with the target mRNA. The sole requirement is that the target mRNA have the following sequence of two bases: 51-UG-31. The construction and production of hammerhead ribozymes is well known in the art. Preferably the ribozyme is engineered so that the cleavage recognition site is located near the 5' end of the target gene mRNA, i.e., to increase efficiency and minimize the intracellular-accumulation of non-functional mRNA transcripts.

The ribozymes of the present invention also include RNA endoribonucleases (hereinafter "Cech-type ribozymes") such as the one that occurs naturally in Tetrahymena thermophila known as the IVS, or L-19 IVS RNA, and that has been extensively described by Thomas Cech and collaborators (Zaug, et al., 1984, *Science* 224:574; Zaug and Cech, 1986, *Science,* 231:470; Zaug, et al., 1986, *Nature,* 324:429; published International patent application No. WO 88/04300 by University Patents Inc.). The Cech-type ribozymes have an eight base pair active site which hybridizes to a target RNA sequence whereafter cleavage of the target RNA takes place.

The methods of the present invention encompasses the use of those Cech-type ribozymes which target eight base-pair active site sequences that are present in the target gene. As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (see, e.g., Smithies, et al., 1985, *Nature* 317:230; Thomas and Capecchi, 1987, *Cell* 51:503). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene. However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in targeT-cells in the body. (see generally, Helene, 1991, *Anticancer Drug Des.,* 6:569; Helene, et al., 1992, *Ann. N.Y. Acad. Sci.,* 660:27; and Maher, 1992, *Bioassays* 14:807).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC* triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex. Alternatively, the potential sequences that can be targeted for triple helix formation may be increased by creating a so called "switchback" nucleic acid molecule. Switchback molecules are synthesized in an alternating 51-31, 31-51 manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may be introduced into cells via gene therapy methods that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules useful in the methods of the invention may be prepared by any method known in the art for the synthesis of DNA and RNA molecules, as discussed above. These include techniques for chemically synthesizing oligodeoxyribonucleotides and oligoribonucleotides well known in the art such as for example solid-phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA

Pharmaceutical Composition

For therapeutic utility, a therapeutically-effective amount of LP82 agonist, LP82 antagonist, LP82 polynucleotide, LP82 polypeptide, LP82 functional fragment, LP82 variant, and/or LP82 antibody as well as therapeutically-effective amount of a hematopoietic cytokine or hematopoietic cytokine antibody is administered to a mammal in need thereof in a dose between about 0.1 and 10,000 µg/kg/day. In practicing the methods contemplated by this invention, the LP82 agonists, LP82 antagonists, LP82 polynucleotides, LP82 polypeptides, LP82 functional fragments, LP82 variants, LP82 antibodies, and/or LP82 compositions thereof optionally further comprising hematopoietic cytokine or hematopoietic cytokine antibody can be administered in multiple doses per day, in single daily doses, in weekly doses, or at any other regular interval. The amount per administration and frequency of administration will be determined by a physician and depend on such factors as the nature and severity of the disease, and the age and general health of the patient.

The present invention also provides a pharmaceutical LP82 composition comprising as the active agent an LP82 agonist, LP82 antagonist, LP82 polynucleotide, LP82 polypeptide, LP82 functional fragment, LP82 variant, and/or LP82 antibody, and/or a pharmaceutically acceptable non-toxic salt thereof, and a pharmaceutically acceptable solid or liquid carrier. For example, at least one LP82 agonist, LP82 antagonist, LP82 polynucleotide, LP82 polypeptide, LP82 functional fragment, LP82 variant, and/or LP82 antibody can be admixed with conventional pharmaceutical carriers and excipients, and used in the form of tablets, capsules, elixirs, suspensions, syrups, wafers, parenteral formulations, and the like. The LP82 compositions will contain from about 0.1% to 90% by weight of the active LP82 agonist, LP82 antagonist, LP82 polynucleotide, LP82 polypeptide, LP82 functional fragment, LP82 variant, and/or LP82 antibody, and more generally from about 10% to 30%. The LP82 compositions may contain common carriers and excipients such as corn-starch or gelatin, lactose, sucrose, microcrystalline cellulose, kaolin, mannitol, dicalcium phosphate, sodium chloride, and alginic acid.

As a general proposition, the total pharmaceutically effective amount of a LP82 agonist, LP82 antagonist, LP82 polynucleotide, LP82 polypeptide, LP82 functional fragment, LP82 variant, and/or LP82 antibody, or hematopoietic cytokine or hematopoietic cytokine antibody administered parenterally to a patient per dose will be in the range of about 1 µg/kg/day to 10 mg/kg/day, particularly 2 mg/kg/day to 8 mg/kg/day, more particularly 2 mg/kg/day to 4 mg/kg/day, even-more particularly 2.2 mg/kg/day to 3.3 mg/kg/day, and finally 2.5 mg/kg/day, although, as noted above, this will be subject to therapeutic discretion. More preferably, this dose is at least 0.01 mg/kg/day. If given continuously a LP82 agonist, LP82 antagonist, LP82 polynucleotide, LP82 polypeptide, LP82 functional fragment, LP82 variant, and/or LP82 antibody and/or hematopoietic cytokine or hematopoietic cytokine antibody is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing a LP82 agonist, LP82 antagonist, LP82 polynucleotide, LP82 polypeptide, LP82 functional fragment, LP82 variant, and/or LP82 antibody and/or hematopoietic cytokine or hematopoietic cytokine antibody may be administered orally, rectally, intracranially, parenterally, intracisternally, intravaginally, intraperitoneally, topically (as by powders, ointments, drops or transdermal patch), transdermally, intrathecally, bucally, or as an oral or nasal spray. By "pharmaceutically acceptable carrier" is meant a non-toxic solid, semisolid or liquid filler, diluent, adjuvant, encapsulating material or formulation auxiliary of any type. The term "parenteral" as used herein includes, but is not limited to, modes of administration which include intravenous, intramuscular, intraperitoneal, intrasternal, subcutaneous and intra-articular injection, infusion and implants comprising a LP82 agonist, LP82 antagonist, LP82 polynucleotide, LP82 polypeptide, LP82 functional fragment, LP82 variant, and/or LP82 antibody.

The compounds can be formulated for oral or parenteral administration. A preferred parenteral formulation for subcutaneous administration would comprise a buffer (phosphate, citrate, acetate, borate, TRIS), salt (NaCl, KCl), divalent metal (Zn, Ca), and isotonicty agent (glycerol, mannitol), detergent (Polyoxyethylene sorbitan fatyy acid esters, poloxamer, ddicusate sodium, sodium lauryl sulfate), antioxidants (ascorbic acid), and antimicrobial agent (phenol, m-cresol, alcohol, benzyl alcohol, butylparben, methylparaben, ethylparaben, chlorocresol, phenoxyethanol,phenylethyl alcohol, propylparaben.

For intravenous (IV) use, a LP82 agonist, LP82 antagonist, LP82 polynucleotide, LP82 polypeptide, LP82 functional fragment, LP82 variant, and/or LP82 antibody and/or hematopoietic cytokine or hematopoietic cytokine antibody is administered in commonly used intravenous fluid(s) and administered by infusion. Such fluids, for example, physiological saline, Ringer's solution or 5% dextrose solution can be used.

For intramuscular preparations, a sterile formulation, preferably a suitable soluble salt form of a LP82 agonist, LP82 antagonist, LP82 polynucleotide, LP82 polypeptide, LP82 functional fragment, LP82 variant, and/or LP82 antibody and/or hematopoietic cytokine or hematopoietic cytokine antibody such as the hydrochloride salt, can be dissolved and administered in a pharmaceutical diluent such as pyrogen-free water (distilled), physiological saline, or a 5% glucose solution. A suitable insoluble form of the compound may be prepared and administered as a suspension in an aqueous base or a pharmaceutically acceptable oil base, e.g. an ester of a long chain fatty acid such as ethyl oleate.

A LP82 agonist, LP82 antagonist, LP82 polynucleotide, LP82 polypeptide, LP82 functional fragment, LP82 variant, and/or LP82 antibody and/or hematopoietic cytokine or hematopoietic cytokine antibody is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773.919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167 (1981), and R. Langer, *Chem. Tech.* 12:98 (1982)), ethylene vinyl acetate (R. Langer et al., Id.) or poly-D-(−)-3-hydroxybutyric acid (EP 133,988). Other sustained-release compositions also include liposomally entrapped modified LP82 polypeptides and/or fragments thereof and/or variants thereof. Such liposomes are prepared by methods known per se: DE 3,218,121; EP 52,322; EP 36,676; EP 88,046; EDP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal therapy.

For parenteral administration, in one embodiment, the LP82 agonist, LP82 antagonist, LP82 polynucleotide, LP82 polypeptide, LP82 functional fragment, LP82 variant, and/or LP82 antibody and/or hematopoietic cytokine or hematopoietic cytokine antibody may be formulated generally by mixing it at the desired degree of purity, in a unit dosage injectable form (solution, suspension, or emulsion), with a pharmaceutically acceptable carrier (i.e., one that is non-toxic to recipients at the dosages and concentrations employed and is compatible with other ingredients of the formulation). Preferably, the formulation does not include oxidizing agents and other compounds that are known to be deleterious to polypeptides.

Generally, the formulations are prepared by contacting LP82 agonist, LP82 antagonist, LP82 polynucleotide, LP82 polypeptide, LP82 functional fragment, LP82 variant, and/or LP82 antibody and/or hematopoietic cytokine or hematopoietic cytokine antibody uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

A LP82 agonist, LP82 antagonist, LP82 polynucleotide, LP82 polypeptide, LP82 functional fragment, LP82 variant, and/or LP82 antibody and/or hematopoietic cytokine or hematopoietic cytokine antibody is typically formulated in such vehicles at a concentration of about 0.1 mg/ml to 100 mg/ml, preferably 1–10 mg/ml, at a pH of about 3 to 8. It will be understood that the use of certain of the foregoing excipients, adjuvants, carriers, or stabilizers will result in the formation of salts of the particular active ingredient(s).

Compositions to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial, subsequently sealed, having a stopper pierceable by a hypodermic injection needle.

Pharmaceutically useful LP82 compositions and hematopoietic cytokine compositions ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution of one of a LP82 composition, and the resulting mixture is lyophilized. The infusion solution is prepared by reconstituting the lyophilized polypeptide using bacteriostatic water for injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Combination Therapies

In addition the therapeutic methods of the present invention may also be employed, alone or in combination with other cytokines, soluble Mpl receptor, hematopoietic factors, interleukins, growth factors or antibodies, preferably in combination with hematopoietic cytokines as defined herein, in the treatment of hematopoietic disease states. It is anticipated that the inventive therapeutic methods will prove useful in treating some forms of thrombocytopenia, anemia, leukemia, bone marrow trans and in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with at least one LP82 agonist, LP82 antagonist, LP82 polynucleotide, LP82 polypeptide, LP82 variant, and/or LP82 antibody. Additional exemplary cytokines or hematopoietic factors for such co-administration include IL-1 alpha, IL-1 beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-22, IL-24, colony stimulating factor-1 (CS F-1), M-CSF, SCF, GM-CSF, granulocyte colony stimulating factor (G-CSF), EPO, interferon-alpha (IFN-alpha), consensus interferon, IFN-beta, IFN-gamma, thrombopoietin (TPO), angiopoietins, for example, Ang-1, Ang-2, Ang-4, Ang-Y, the human angiopoietin-like polypeptide, vascular endothelial growth factor (VEGF), angiogenin, bone morphogenic protein-1 through 15, bone morphogenic protein receptor 1a, bone morphogenic protein receptor 1b, brain derived neurotrophic factor, ciliary neutrophic factor, ciliary neutrophic factor receptor, epidermal growth factor, epithelial-derived neutrophil attractant, fibroblast growth factor 4 through 10, fibroblast growth factor acidic, fibroblast growth factor basic, glial cell line-derived neutrophic factor receptors, heparin binding epidermal growth factor, hepatocyte growth factors, hepatocyte growth factor receptors, insulin-like growth factor 1, insulin-like growth factor receptors, insulin-like growth factor 11, insulin-like growth factor binding protein, keratinocyte growth factor, leukemia inhibitory factor, leukemia inhibitory factor receptor a, nerve growth factor, nerve growth factor receptors, neurotrophin-3, neurotrophin-4, placenta growth factor, placenta growth factor 2, platelet-derived endothelial cell growth factor, platelet derived growth factors including, but not limited to, platelet derived growth factor A chain, platelet derived growth factor AA, platelet derived growth factor AB, platelet derived growth factor B chain, platelet derived growth factor BB, and platelet derived growth factor receptors, pre-B cell growth stimulating factor, stem cell factor receptor, tumor necrosis factors, including TNFO, TNFI, TNF2, transforming growth factor u, transforming growth factor P, transforming growth factor P 1, transforming growth factor P 1.2, transforming growth factor P2, transforming growth factor P3, transforming growth factor P5, latent transforming growth factor P1, transforming growth factor P binding protein 1, transforming growth factor P binding protein 2, transforming growth factor P binding protein 3, tumor necrosis factor receptor type 1, tumor necrosis factor receptor type 2, urokinase-type plasminogen activator receptor, vascular endothelial growth factor, and chimeric proteins and biologically or immunologically active fragments thereof. It may further be useful to administer, either simultaneously or sequentially (either before or after), an effective amount of a soluble mammalian Mpl receptor, which appears to have an effect of causing megakaryocytes to fragment into platelets once the megakaryocytes have reached mature form. Thus, administration of an LP82 composition in combination with at least one of the additional factors provided hereinabove in combination with administration of the soluble Mpl receptor (to inactivate the ligand and allow the mature megakaryocytes to produce platelets) is expected to be a particularly effective means of stimulating platelet production. The dosage recited above would be adjusted to compensate for such additional components in the therapeutic composition. Administration in combination with one or more further therapeutic agents includes simultaneous (concurrent) and consecutive administration in any order. Progress of the treated patient can be monitored by assays provided herein or otherwise known in the art.

The following examples more fully describe the present invention. Those skilled in the art will recognize that the particular reagents, equipment, and procedures described are merely illustrative and are not intended to limit the present invention in any manner.

EXAMPLES

Example 1

LP82 Transgenic Rodent Development

A. Transgene construction.

Polymerase chain reaction (PCR) primers were synthesized and used to amplify the LP82 coding region from a plasmid containing the full length coding region plus surrounding sequences:

```
                                                (SEQ ID NO: 4)
5'TTGGCGCGCCATCCACCATGAAAGCCTCTAGTCTTGCC 3'

(SEQ ID NO: 5)
5'TAGCGGCCGCTACTTGTCGTCGTCATCCTTGTAGTCTTCTGTCTCCT
CCATCCATTGCAG 3'
```

The 5' primer (SEQ ID NO: 4) incorporated an Asc I restriction enzyme site (underlined) and Kozak sequence while the 3' primer (SEQ ID NO: 5) incorporated a Not I restriction enzyme site to facilitate cloning. The amplified ~0.7 kb fragment was ligated into the multiple cloning site (Asc I-Not I) of plasmid pK409, a derivative of the pFastBac expression vector (Gibco BRL). The constructed vector with LP82Flag [pEW1943] was subsequently digested with Asc I-Xho I and cloned into pLIV7 (provided by John Taylor, Gladstone Institutes) at the Mlu I-Xho I sites generating plasmid pLIV7/LP82Flag-pEW3033.

Those of skill in the art can readily design numerous alternative PCR primers for amplifying the LP82 gene in human DNA or other mammalian DNA using the nucleotide sequence of LP82, the surrounding sequence as shown in SEQ ID NO: 1 and techniques standard in the art.

B. Transgenic Animal Development

Transgenic mice were generated using established techniques (Hogan, B. et al. (1986) *Manipulating the Mouse Embryo: A Laboratory Manual*. Cold Spring Harbor Laboratory, NY as modified by Fox and Solter (*Mol. Cell. Biol.* 8: 5470, 1988). Briefly, a 6.4 kb DNA fragment encompassing the human apolipoprotein E (hApoE) gene promoter-5'hApoE untranslated region-LP82/FLAG-hepatic control region (HCR) fusion gene was excised from plasmid pLIV7-LP82 by digestion with Sal I and Spe I and purified by gel electrophoresis and glass bead extraction. The purified DNA fragment encompassing the hApoE gene promoter-5' hApoE untranslated region-LP82-HCR fusion gene was microinjected into the male pronuclei of newly fertilized one-cell-stage embryos (zygotes) of the FVB/N strain. The embryos were cultured in vitro overnight to allow development to the two-cell-stage. Two-cell embryos were then transplanted into the oviducts of pseudopregnant ICR strain mice to allow development to term. To test for the presence of the transgene in the newborn mice, a small piece of toe was removed from each animal and digested with proteinase K to release the nucleic acids. A sample of the toe extract was subsequently subjected to PCR analysis using primers specific for the hApoE untranslated region to identify transgene-containing mice. Five founder transgenic mice were identified. Each of these founders was bred to produce F1 and F2 progeny. Many of the transgenic pups die within the first few days after birth, they have smaller body size and wrinkled skin with a thickened epidermis. Non-transgenic mice in a litter were noticeably larger than the transgenic mice and were removed from the litter to better enable survival of the transgenic mice. Transgenic mice have about 2 fold greater numbers of CFU-GEMM in the spleen than do wild type mice (see Example 2).

Example 2

LP82 Transgenic Mice Hematopoietic Progenitor Cells

Mouse bone marrow cells and splenocytes were isolated from LP82 transgenic mice and age-matched wild type mice. Then, $1 \times 10^5$ mononuclear cells from the bone marrow or $1 \times 10^6$ mononuclear cells from the spleen of each mouse were cultured in methylcellulose (Stem Cell Technologies) in the presence of 0.1 mM hemin using standard protocol known in the art. Colony growth was stimulated with the following combinations of recombinant growth factors (200 ng/ml): Medium A: Epo (1 U/ml, R&D System) plus SCF (50 ng/ml, R&D System) and PWM-SCM (conditioned medium 5%, Stem Cell Technologies) or Medium B: Epo 1 U/ml. After culturing the cells at 37° C. for seven days, the different types of colonies were counted from each dish under an inverted microscope. Group mean and SD were calculated. The data in Table 2 below represent the average from 20 mice in each group plus or minus the standard deviation. The bone marrow values are per femur, the spleen values are per spleen.

TABLE 2

LP82 Transgenic Mice Hematopoietic Progenitor Cells

|  | TRANSGENIC | WILD TYPE |
|---|---|---|
| CFU-GM/femur | | |
| Medium A | 26258 ± 5397 | 22781 ± 6177 |
| Medium B | 14660 ± 5458 | 12395 ± 870 |
| CFU-GM/spleen | | |
| Medium A | 10389 ± 7510 | 9257 ± 4208 |
| Medium B | 21548 ± 3716 | 13478 ± 4783 |
| BFU-E/femur | | |
| Medium A | 3815 ± 1387 | 3796 ± 1503 |
| Medium B | 4157 ± 1363 | 3427 ± 373 |
| BFU-E/spleen | | |
| Medium A | 2578 ± 2215 | 2625 ± 2130 |
| Medium B | 4592 ± 882 | 1820 ± 451 |
| CFU-GEMM/femur | | |
| Medium A | 3904 ± 916 | 1649 ± 551 |
| Medium B | 2139 ± 450 | 1005 ± 230 |
| CFU-GEMM/spleen | | |
| Medium A | 2474 ± 2306 | 1136 ± 1044 |
| Medium B | 3444 ± 944 | 1775 ± 645 |

The LP82 transgenic mice had about two fold greater numbers of CFU-GEMM in both bone marrow and spleen in both types of conditions tested. The presence of LP82 also led to increase in the number BFU-E and CFU-GM cells in some conditions.

Example 3

Increased HCT Recovery in LP82 Transgenic Mice

Figure 2:
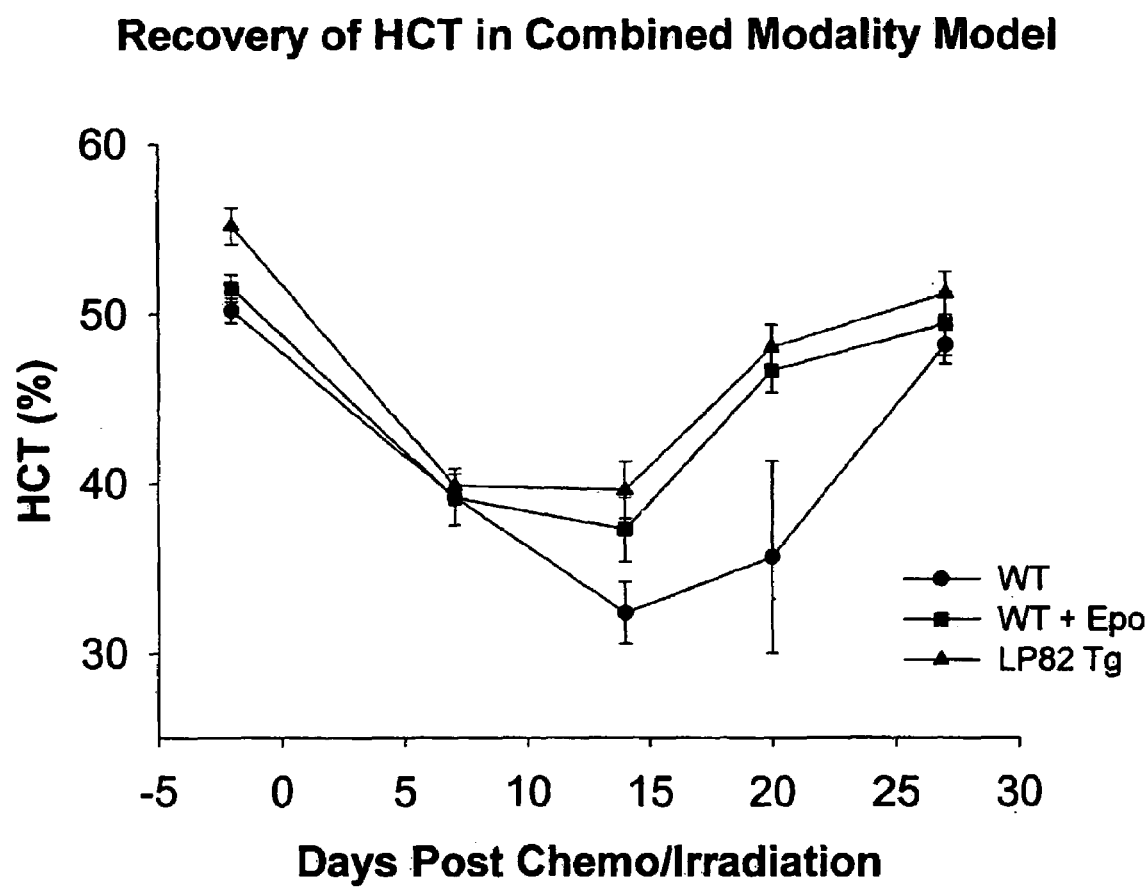
FIG. 2 illustrates the hematocrit recovery in a mouse chemotherapy/irradiation model. The values represent the mean +/− SEM.

Ten to twelve week-old LP82 transgenic mice and age matched wild type mice were exposed to myelosuppresive therapy of 400 rads total body irradiation followed by a single intraperitoneal injection of 0.8 mg carboplatin as described by Kaushansky, et al. (*J. Clin. Invest* 96:1883, 1996). For a comparison group, recombinant human Epo was injected 20 IU daily s.c. for 12 days. Blood counts were performed on 50 µl samples obtained by retro-orbital route, using a Hemavet 1500 hematology analyzer (CDC Technologies). As shown in FIG. 2, LP82 transgenic mice had significantly increased recovery of hematocrit (HCT) in comparison to wild type mice indicating that LP82 expression enhances the recovery of RBC and HCT following myelosuppressive therapy.

Example 4

LP82 Increases Cycling Status of CFU-GEMM

Bone marrow cells and splenocytes were isolated from ten LP82 transgenic mice and ten wild type mice. Individual samples from each mouse were pulsed for 20 to 30 minutes with high specific activity tritiated-thymidine prior to plating cells in methylcellulose culture medium in the presence of hemin. A control sample of cells was not pulsed with tritiated-thymidine. This analysis allowed an estimation of the cycling status of the progenitor cells (i.e., percentage progenitor cells in S-phase of the cell cycle) at the time they are removed from the mice. Only those cells in S-phase of the cell cycle would be labeled with the tritiated-thymidine. The tritiated-thymidine lethally irradiates those cells that incorporate it, thus making them unable to divide. The difference between the number of colonies present in the control sample minus the number remaining alive in the tritiated sample is equal to the number of cells in S-phase prior to labeling. Colony growth was stimulated with Epo (2 U/ml), SCF (50 ng/ml), PWM-SCM (5%) and hemin. LP82 transgenic mice had statistically significant increase in the cycling status of CFU-GEMM as shown in Table 3 below

TABLE 3

LP82 Increased Cycling Status of CFU-GEMM

|  | Percentage CFU-GEMM in S-phase |
|---|---|
| Wild type mice bone marrow | 8 ± 11 |
| LP82 Transgenic mice bone marrow | 58 ± 8 |
| Wild type mice spleen | 4 ± 13 |
| LP82 Transgenic mice spleen | 57 ± 20 |

Example 5

Administration of LP82 to Mice Increases Numbers of CFU-GEMM

Groups of eight-to-ten-week-old female BDF1 mice (Harlan, Indianapolis) were used in the study. Mice were bled 7 days prior to the study via retro-orbital route to obtain baseline blood cell counts. Groups were injected twice daily (s.c.) for eleven days with the following:

1001-3: diluent (PBS+0.5% homologous mouse serum)
2001-3: LP82 in diluent (5 µg per injection)
3001-3: Epo in diluent (10 units per injection)
4001-3: LP82+Epo in diluent (same amounts as above)
5001-3: SCF (1.5 µg/injection)+Epo (10 units/injection) in diluent
6001-3: LP82+Epo+SCF in diluent (same amounts as above)

Bone marrow cells from the mice were then harvested and cultured in methylcellulose-based medium in the presence of 30% fetal calf serum and hemin. Colony growth was stimulated with Epo (2 U/ml, R&D System), SCF (50 ng/ml, R&D System) and IL-3(R&D System). The colonies of BFU-E, CFU-GM and CFU-GEMM cells were scored under an inverted microscope. The total number of each kind of progenitors in one femur was calculated for each mouse.

As shown in Table 4 below, LP82 alone or in combination with other cytokines significantly increased the numbers of mouse CFU-GEMM in vivo (per femur). Significant increases of CFU-GM cells in LP82+Epo+SCF treated mice (compared to Epo+SCF) and BFU-E cells in LP82+Epo (compared to Epo) is treated mice were also observed. The data support that LP82 acts on hematopoietic progenitor cells and may be used to treat anemia, thrombocytopenia and neutropenia, e.g., secondary to cancer chemotherapy.

The mice in the study were also bled at day 8 and 12 post injection. The blood samples were analyzed on a Hemavet 1500 blood analyzer machine with settings optimized for mouse blood. The results are shown in Table 5 below as percent increase from baseline, calculated with the following formula:

(average change of experimental group−average change of diluent group/pretreatment average of experimental group)×100.

The data demonstrate that percent increases from baseline were higher for LP82+SCF+Epo for all parameters tested at day 12. Larger increases were observed at day 8 for platelets, white blood cells and neutrophils for LP82+Epo+SCF compared to Epo+SCF. This is consistent with knowledge in the art that effects of SCF administration are transient, with a peak at 7–8 days (Ulich, et al., Blood, 78:645–50, 1991).

TABLE 4

|  | BFU-E | CFU-GM | CFU-GEMM | Total CFC |
|---|---|---|---|---|
| Diluent, 1001 | 6395.2 | 73434.5 | 4190.0 | 84019.6 |
| Diluent, 1002 | 6897.9 | 63230.3 | 3257.3 | 73385.5 |
| Diluent, 1003 | 6574.7 | 68095.5 | 3287.4 | 77957.6 |
| LP82, 2001 | 5974.3 | 65478.6 | 7169.2 | 78622.1 |
| LP82, 2002 | 5910.8 | 70085.0 | 8162.5 | 84158.3 |
| LP82, 2003 | 2814.6 | 72711.7 | 6098.4 | 81624.8 |
| Epo, 3001 | 2436.0 | 63539.0 | 1827.0 | 67802.0 |
| Epo, 3002 | 2362.7 | 46150.7 | 2205.2 | 50718.5 |
| Epo, 3003 | 2378.4 | 55999.9 | 3675.7 | 62054.0 |
| LP82 + Epo, 4001 | 3528.2 | 65998.4 | 4565.9 | 74092.5 |
| LP82 + Epo, 4002 | 4273.2 | 61960.7 | 4006.1 | 70239.9 |
| LP82 + Epo, 4003 | 4334.2 | 51781.9 | 4334.2 | 60450.2 |
| SCF + Epo, 5001 | 2776.0 | 53669.5 | 1388.0 | 57833.5 |
| SCF + Epo, 5002 | 1149.6 | 51539.3 | 3257.1 | 55946.0 |
| SCF + Epo, 5003 | 2875.6 | 58333.6 | 3081.0 | 64290.2 |
| LP82 + SCF + Epo, 6001 | 2599.1 | 73009.9 | 3307.9 | 78916.9 |
| LP82 + SCF + Epo, 6002 | 3874.8 | 81113.1 | 7491.3 | 92479.3 |
| LP82 + SCF + Epo, 6003 | 2235.3 | 63706.6 | 6482.4 | 72424.4 |

TABLE 5

| Percent above baseline at day 8 | | |
|---|---|---|
|  | Epo + SCF | LP82 + Epo + SCF |
| Hematocrit | 29 | 34 |
| RBC | 37 | 47 |
| Hemoglobin | 42 | 81 |
| Platelets | 40 | 86 |
| WBC | 161 | 741 |
| Neutrophils | 292 | 992 |

| Percent above baseline at day 12 | | | | |
|---|---|---|---|---|
|  | LP82 | Epo | LP82 + Epo | Epo + SCF | LP82 + Epo + SCF |
| HCT | 4.6 | 58 | 48 | 48 | 63 |
| RBC | 5.2 | 59 | 52 | 58 | 71 |
| Hb | 3.8 | 45 | 41 | 35 | 47 |
| PLT | 1.5 | 2.1 | 8.8 | 28 | 33 |
| WBC | 41 | 53 | 49 | 42 | 54 |
| NE | 42 | 53 | 76 | 104 | 156 |

Example 6

In Vitro Testing for Hematopietic Modulators

A. Human Megakaryocyte Assay

LP82 polypeptides can be assayed for the ability to stimulate development of human megakaryocytes from CD34+ progenitor cells. CD34+ selected cells are obtained from bone marrow as described (Hokom, M. et al., *Molecular Biology of Haematopoiesis* 3:15, 1994) and incubated in Iscove's modified Dulbecco's medium (IMDM; GIBCO, Grand Island, N.Y.) with 2 mM Glutamine, 2-mercaptoethanol ($10^{-4}$ M), 1% bovine serum albumin, low density lipoprotein (40 µg/ml, Sigma); bovine pancreatic insulin (10 µg/ml), human transferrin (200 µg/ml), human recombinant thrombopoietin (50 ng/ml, R&D System); human recombinant stem cell factor (50 ng/ml, R&D Systems) and plus or minus isolated LP82 (200 ng/ml). CD34+cells are plated at 3300 cells/ml final concentrations on 2 well chamber slides purchased from StemCell Technologies (Vancouver, Canada). Cells are incubated at 37° C. for 12 days in humidified boxes in 5% $CO_2$ in air. The cells are then fixed directly to the culture wells with 1:3 methanol:acetone solution, and incubated with a monoclonal antibody, anti-GPIIb/IIIa, (StemCell Technologies). The immune reaction is developed with biotin-conjugated goat-anti-mouse Ig G followed by avidin-alkaline phosphatase conjugate, identified by pink color, and counted with an inverted-phase microscope at 100× magnification. In the absence of LP82, there were 47 megakaryocytic colonies observed, in the presence of LP82. (200 ng/ml) there were 65 megakaryocytic colonies observed.

B. Assay for Liquid Bone Marrow Culture

CD34+ human bone marrow cells from Poietics, Inc. are plated in polypropylene V-bottomed 96 well plates at 10,000 cells/well with three wells/group. Stem Cell Factor (SCF) is used at 10 ng/ml, interleukin-3 (IL-3) is used at 0.1 ng/ml, erythropoietin (EPO) is used at 1 U/ml and LP82 is used at 400 ng/ml. The following cytokine conditions are tested in IMDM/30% FBS+antibiotics:

1. SCF/IL-3/(±LP82)
2. IL-3/EPO/(±LP82)
3. SCF/IL-3/EPO/(±LP82)
4. SCF/IL-3/MCSF*
5. SCF/IL-3/EPO/TGFβ*

* MCSF is macrophage colony stimulating factor, TGFβ is transforming growth factor beta.

Sample 1, SCF+IL-3 is a negative control with minimal growth expected in the absence of an additional factor (e.g., LP82). Sample 2, IL-3+EPO is a negative control with minimal growth expected in the absence of an additional growth factor. Sample 3, SCF+IL-3+EPO is expected to produce strong erythroid growth and/or differentiation in the absence of an additional factor and also demonstrates the amount of erythroid growth and/or differentiation in excess of that observed when SCF+IL-3 or IL-3+EPO are used in the absence of the third factor (plus or minus LP82). Sample 4, SCF+IL-3+MCSF is used to demonstrate detectable monocytic growth and/or differentiation in comparison to using SCF+IL-3 in the absence of MCSF (plus or minus LP82). Sample 5, SCF+IL-3+EPO+TGF β is used to demonstrate modulation of erythroid growth and/or differentiation in comparision to using SCF+IL-3+EPO in the absence of TGFβ (plus or minus LP82).

Cultures are incubated at 37° C., 5% $CO_2$, 95% humidity for 10 days with a breathable sealing membrane to prevent evaporation. Feeding occurs at days 4 and 7 by replacing 400 µl of the medium with fresh medium. At day 10 the cells are transferred to V-bottomed plates and stained for CD14 (FITC) and CD36 (PE) cell surface antigens. The cells are centrifuged and incubated 15 minutes at 4° C. with 50 µg/ml human IgG (Sigma). Monocytes are CD14+, cells of the erythrocyte lineage are CD36+, cells that are negative for both CD14 and CD36 are termed "undefined" and may subsequently differentiate into monocytes or erythrocytes.

Diagnostic antibodies, αCD14-FITC (Miltenyi Biotec) for monocytes and αCD36-PE (BD Pharmingen) for erythroid cells are added for an additional 15 minutes. After a wash (phosphate buffered saline, 0.1% bovine serum albumin), cells are transferred to 12×75 mm tubes in a final volume of 1 ml containing 0.1 ml FlowCount Fluorospheres (Coulter). Cells are then acquired on a flow cytometer based on constant FlowCount Fluorosphere numbers, (e.g. 5000). Analysis of data is accomplished by determining the number of cells of each lineage that are present in each well which is calculated based on the known number of fluorospheres in the sample. Numbers of total cells, monocytic cells, erythroid cells, and undefined lineages (CD14- and CD36-minus) are determined. Data are subjected to statistical analysis using JMP 4 software. Unknowns are compared to negative controls using Dunnet's test at p=0.01. Data are presented below in Table 6.

TABLE 6

| SCF/IL3 | Cells | Moncytes | Erythroid | undefined |
|---|---|---|---|---|
| | | Mean | | |
| Control | 64967 | 21467 | 6533 | 43033 |
| LP82 | 57567 | 17467 | 6000 | 39833 |
| EPO | 400067 | 14833 | 102833 | 355300 |
| MCSF | 79067 | 45967 | 5967 | 32733 |
| | | Standard Deviation | | |
| Control | 4143 | 850 | 1750 | 4236 |
| LP82 | 5877 | 3325 | 557 | 4050 |
| EPO | 34676 | 1193 | 12806 | 30616 |
| MCSF | 12171 | 9042 | 208 | 3201 |
| IL3/EPO | Cells | Monocytes | Erythroid | undefined |
| | | Mean | | |
| Control | 219933 | 12800 | 31767 | 198033 |
| LP82 | 240333 | 13467 | 44033 | 211700 |
| SCF | 400067 | 14833 | 102833 | 355300 |
| | | Standard Deviation | | |
| Control | 14810 | 2307 | 5677 | 13759 |
| LP82 | 22472 | 1845 | 9678 | 19721 |
| SCF | 34676 | 1193 | 12806 | 30616 |
| SCF/IL3/EPO | Cells | Monocytes | Erythroid | undefined |
| | | Mean | | |
| Control | 400067 | 14833 | 102833 | 355300 |
| LP82 | 608900 | 21400 | 191100 | 524800 |
| TGFb | 280767 | 7067 | 17300 | 271500 |
| | | Standard Deviation | | |
| Control | 34676 | 1193 | 12806 | 30616 |
| LP82 | 20223 | 2404 | 15556 | 8910 |
| TGFb | 33954 | 907 | 2706 | 34785 |

The data demonstrate that LP82, in the presence of stem cell factor, interleukin 3, and erythropoetin, induces greater numbers of total, erythroid and undefined (non-erythroid or monocytic) cells than the negative control.

C. LP82 Increases the Numbers of CFU-GEMM

CD34+ cells were seeded into methylcellulose culture or Agar culture medium (Stem Cell Technologies) using standard procedures. Colony growth was stimulated with the following combinations of recombinant growth factors with and without LP82 (at 200 ng/ml): (1) Epo (2 U/ml) plus SCF (50 ng/ml) and (2) Epo+SCF+IL-3 (10 ng/ml). All the commercially available cytokines were purchased from R&D Systems (Minneapolis, Minn.). After culture at 37° C. for 2 weeks, the different types of colonies were counted from each dish under an inverted microscope. Results are shown in Table 7 below, LP82 significantly increased the numbers of CFU-GEMM that ultimately differentiate into red blood cells, granulocytes, monocytes, and platelets and slightly increased numbers of CFU-GM.

TABLE 7

LP82 Increased Numbers of Human CFU-GEMM

| Cytokine combinations | CFU-GEMM per 1000 cells |
|---|---|
| Epo + SCF | 3 |
| Epo + SCF + LP82 | 7 |
| Epo + SCF + IL-3 | 9 |
| Epo + SCF + IL-3 + LP82 | 18 |

Example 7

Additional in vivo Testing in Normal Mice for Hematopietic Modulators

A. Assays for Recovery of Blood Cells After Bone Marrow Transplantation

Bone marrow (BM) is harvested by gentle flushing the hind limbs of normal 8- to 10-week-old Balb C mice (purchased from Harlan Sprague Dawley, Indianapoils, Ind.) using RPMI medium containing 10% fetal calf serum. For some experiments, donor mice are pretreated with 5-fluorouracil (5-FU) at 150-mg/kg-body weight intraperitoneally (IP) 3 days before harvesting BM for infusion. After total body irradiation with about 10.8 Gy ($^{137}$Cs at 126cGy/min, split dose with a minimum of 3 hours between doses), $1 \times 10^6$ bone marrow cells are injected intravenously (IV) into lethally irradiated mice. LP82 (250 μg/kg body weight) is diluted in PBS and injected subcutaneously in 0.2-ml volume daily starting on the same day as irradiation and infusion of donor bone marrow cells. Control mice received the same volume of PBS. Administration of LP82 polypeptides occurs during days 0–17. Mice are weighed every 4 days during the post-transplantation period. Hematologic analysis of leukocyte cell counts and platelet counts are performed on orbit bleeds on a CDC Hemavet™ machine. Blood smears are stained with Wright-Giemsa using standard methods and examined at 100× for differentiation analysis. Hematocrits are performed by spinning capillary tubes for 5 minutes in a Model MB Micro-Capillary Centrifuge. Accordingly, LP82 polypeptides may be used to accelerate recovery of peripheral blood cell counts.

B. Assays for Recovery of Blood Cells After Combined Chemo-/Radiation Therapy

Eight- to ten-week old BDF1 mice (Harlan Sprague Dawley) are administered carboplatin at 60-mg/kg body weights intraperitoneally (IP) 1 hour before sub-lethal irradiation (0.5 Gy total body irradiation for 20–22 mg mouse). LP82 polypeptide (with or without EPO or G-CSF) is injected subcutaneously in a 0.2 ml volume daily starting on the same day as irradiation. Negative control mice receive the same volume of PBS as the treated mice. LP82 polypeptide administration lasts for 17 days. The mice are analyzed at various days post-radiation. Mice are weighed every 2 to 4 days during the post-radiation period. Hematologic analysis of leukocyte cell counts and platelet counts are performed on orbit bleeds on a CDC Hemavet™ machine. Blood smears are stained with Wright-Giemsa using standard methods and examine at 100× for differentiation analysis. Hematocrit measurements are performed by spinning capillary tubes for 5 minutes in a Model MB Micro-Capillary Centrifuge. LP82 polypeptides may be useful in accelerating recovery of peripheral blood cell counts after chemotherapy and/or radiation therapy.

C. Assays for Treatment of Anemia

Various animal models of anemia and hematopoietic disorder are known in the art and generally accepted as being indicative of the anemic condition. For instance, the exhypoxic polycythemic mouse bioassay may be used to quantify the incorporation of 5' Fe (iron) into newly synthesized red blood cells as a measure of the increase in erythropoiesis in mice in response to an exogenously administered test sample (e.g., a putative LP82 agonist, LP82 antagonist, LP82 polynucleotide, LP82 polypeptide, LP82 fragment, LP82 variant, and/or LP82 antibody). The assay, as described in WO/0024893 (herein incorporated by reference), is a modification of the method of Cotes and Bangham (*Nature* 191:1065 (1961)).

The test agent(s) may be administered by any of several routes of administration (e.g. i.v., s.c., i.p., or by minipump or cannula) and suitable test animals include normal mice as well as LP82 transgenic mice similar to those described in Example 1. Controls for non-specific effects for these treatments are done using vehicle with or without the active agent of similar composition in the same type animal monitoring the same parameters.

Example 8

Proliferation and Cytokine Secretion of LP82 Expressing Splenocytes Upon Antigenic Stimulation Flat bottom 96 well plates are coated with 100 µl media (RPMI, 10% FBS) containing 5 µg/ml α-CD3 per well. Plates are coated for 1.5 hrs. at 37° C., aspirated, and washed 2× in PBS. Then, $4 \times 10^5$ spleen cells in a 100 µl volume of media are added to each well and plates are incubated for 48 hrs. at 37° C. After plates are centrifuged at 1200 rpm for 5 min., 100 µl of supernatant from each well is removed and transferred to 96-well U-bottom plates of which 10 µl is used for a cytokine secretion immunoassay according to standard procedures. The remainder of cells are pulse-labeled with 1 µCi of $^3$H-thymidine/well and incubated for another 24 hrs. prior to counting. In addition to activation of splenocytes by anti-CD3, other stimuli can be tested in the same manner. Preferred stimuli to test include dilutions of 2.5 ng/ml IL-2, dilutions of 8 µg/ml ConA, dilutions of PMA with 1 µM ionomycin, and 100 µg/ml LPS.

Example 9

Exposure of LP82 Transgenic Mice to Sub-Lethal Doses of Radiation

Wild type and transgenic mice of both genders are irradiated at 600 cGy. The mice are analyzed at 3, 7, 10, 14, 21, 28 days post-radiation. Mice are weighed every 2 days during the post-radiation period. Hematologic analysis of leukocyte cell counts and platelet counts are performed on orbit bleeds on a CDC Mascot™ machine. Blood smears are stained with Wright-Giemsa using standard methods and examine at 100× for differentiation analysis. Peripheral blood hematocrits are performed by spinning capillary tubes for 5 minutes in a Model MB Micro-Capillary Centrifuge. LP82 may be used to accelerate the recovery of peripheral blood cell counts after exposure to sub-lethal doses of radiation.

By increase of absolute numbers and/or the cycling status of CFU-GEMM cells, LP82 alone or in combination with other cytokines, can be used to treat anemia, thrombocytopenia, neuropenia and other hematopoietic and immune disorders.

Example 10

Large Scale LP82 Polypeptide Purification

Cell culture media containing LP82 (secreted from cells expressing FLIS-tagged-LP82) is concentrated in an Amicon ProFlux M12 tangential filtration system using an Amicon S3Y10 UF membrane. The concentrated media is passed over an immobilized metal-affinity chromatography column (Pharmacia) at a flow rate of 2 ml/min. The column is washed with buffer A (PBS (1 mM potassium phosphate, 3 mM sodium phosphate), 0.15 M NaCl, pH 7.4 containing 50 mM Imidazol) until the absorbance returns to baseline. The bound polypeptides are eluted with a gradient from 100% Buffer A to 55% Buffer A developed over 70 min. The gradient is then stepped to 100% Buffer B (buffer A containing 0.5 M Imidazol) for 20 min. Fractions containing LP82 are pooled and concentrated using an Ultrafree centrifugal filter unit (Millipore, 10 kDa molecular weight cut-off) to 14 ml. This material is passed over a Superdex 75 (Pharmacia, 26/60) sizing column equilibrated with PBS, 0.5 M NaCl, pH 7.4, at a flow rate of 3 ml/min. Fractions containing LP82 are analyzed by SDS-PAGE. The N-termination sequence of LP82 was confirmed on the purified polypeptide using standard techniques.

Example 11

Proliferation of LP82 Splenocytes in a Mixed Lymphocyte Reaction

In a mixed lymphocyte reaction assay, splenocytes from DBA/2 mice (Harlan Sprague Dawley, Indianapolis, Ind.) may be used as stimulator cells after being treated with mitomycin C. The responder cells are splenocytes isolated from C57Bl/6 mice (Harlan Sprague Dawley) transplanted with the LP82 gene or naïve mice. The suspensions of responder T-cells are cultured with allogeneic stimulator lymphocytes. The activating stimulus is the foreign histocompatibility antigen (usually MHC class I or class II molecules) expressed on the allogenic stimulator cells.

In brief, splenocytes from DBA/2 are added to 96-well plates at $1 \times 10^6$ cells per well in RPMI+10% FBS and Pen/Strep. Splenocytes from either age matched C57Bl/6 naïve mice or retroviral expressed LP82 mice are added as responder cells to wells at either 0.5, 1, 2, 4, or $8 \times 10^5$ cells per well. Control wells contained DBA stimulator splenocytes alone or C57Bl/6 responder splenocytes alone. After 72 hours in vitro, wells are pulse labeled with 1 uCi of tritiated thymidine. After 18 hrs, cells are harvested and counted.

We claim:

1. A method of increasing the number of colony-forming unit-granulocyte-erythrocyte-macrophage/monocyte-megakaryocyte (CFU-GEMM) hematopoietic progenitor cells in a mammal in need thereof comprising administering a therapeutically effective amount of an LP82 polypeptide, wherein said LP82 polypeptide is selected from the group consisting of:
   a) a polypeptide comprising residues from 1 through 176 of SEQ ID NO: 2; and
   b) a polypeptide comprising residues from 25 through 176 of SEQ ID NO: 2.

2. A method of increasing the number of red blood cells in a mammal in need thereof comprising administering a therapeutically effective amount of an LP82 polypeptide, wherein said LP82 polypeptide is selected from the group consisting of:
   a) a polypeptide comprising residues from 1 through 176 of SEQ ID NO: 2; and
   b) a polypeptide comprising residues from 25 through 176 of SEQ ID NO: 2.

3. A method of increasing hematocrit in a mammal in need thereof comprising administering a therapeutically effective amount of an LP82 polypeptide, wherein said LP82 polypeptide is selected from the group consisting of:
   a) a polypeptide comprising residues from 1 through 176 of SEQ ID NO: 2; and
   b) a polypeptide comprising residues from 25 through 176 of SEQ ID NO: 2.

4. The method of claim 1 further comprising administering a therapeutically effective amount of at least one hematopoietic cytokine in addition to the LP82 polypeptide.

5. The method of claim 4 wherein the hematopoietic cytokine is administered prior to, simultaneously with, or subsequent to the LP82 polypeptide.

6. The method of claim 4 wherein the at least one hematopoietic cytokine in addition to the LP82 polypeptide is selected from the group consisting of: erythropoietin, thrombopoietin, interleukin-1, interleukin-3, interleukin-4, interleukin-5, interleukin-7, interleukin-9, interleukin-11, granulocyte-colony stimulating factor, granulocyte-macrophage-colony stimulating factor, macrophage-colony stimulating factor and stem cell factor.

7. The method of claim 1 further comprising administering to the mammal a therapeutically effective amount of a chemotherapeutic agent prior to, simultaneously with, or subsequent to the LP82 polypeptide.

8. A method of treating anemia, thrombocytopenia or neutropenia in a mammal comprising the administration to said mammal in need of such treatment a pharmaceutical composition comprising a therapeutically effective amount of an LP82 polypeptide, wherein said LP82 polypeptide is selected from the group consisting of:
   a) a polypeptide comprising residues from 1 through 176 of SEQ ID NO: 2; and
   b) a polypeptide comprising residues from 25 through 176 of SEQ ID NO: 2.

9. The method of claim 8 wherein the method further comprises administration to said mammal a pharmaceutical composition comprising a therapeutically effective amount of at least one hematopoietic cytokine.

10. The method of claim 9 wherein the hematopoietic cytokine is administered prior to, simultaneously with, or subsequent to the administration of the LP82 polypeptide.

11. The method of claim 9 wherein the hematopoietic cytokine is selected from the group consisting of erythropoietin, thrombopoietin, interleukin-1, interleukin-3, interleukin-4, interleukin-5, interleukin-7, interleukin-9, interleukin-11, granulocyte-colony stimulating factor, granulocyte-macrophage-colony stimulating factor, macrophage-colony stimulating factor and stem cell factor.

12. The method of claim 9 wherein the composition comprising the LP82 polypeptide further comprises the hematopoietic cytokine.

13. The method of claim 8 wherein the anemia, thrombocytopenia or neutropenia result from chemotherapy or radiation therapy.

* * * * *